US007572796B2

(12) United States Patent
Schadt et al.

(10) Patent No.: US 7,572,796 B2
(45) Date of Patent: Aug. 11, 2009

(54) SUBSTITUTED INDOLES

(75) Inventors: Oliver Schadt, Rodenbach (DE); Henning Böttcher, Darmstadt (DE); Joachim Leibrock, Pfungstadt (DE); Kai Schiemann, Seeheim-Jugenheim (DE); Timo Heinrich, Groβ-Umstadt (DE); Günter Hölzemann, Seeheim-Jugenheim (DE); Christoph van Amsterdam, Darmstadt (DE); Gerd Bartoszyk, Weiterstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 147 days.

(21) Appl. No.: 10/511,155

(22) PCT Filed: Apr. 11, 2003

(86) PCT No.: PCT/EP03/03806

§ 371 (c)(1),
(2), (4) Date: Oct. 14, 2004

(87) PCT Pub. No.: WO03/087086

PCT Pub. Date: Oct. 23, 2003

(65) Prior Publication Data

US 2005/0153980 A1 Jul. 14, 2005

(30) Foreign Application Priority Data

Apr. 16, 2002 (DE) ................................ 102 17 006

(51) Int. Cl.
*A61K 31/497* (2006.01)
*C07D 405/00* (2006.01)

(52) U.S. Cl. .................. 514/254.09; 514/323; 544/376; 546/268.4

(58) Field of Classification Search ................. 544/376; 546/268.4; 514/254.09, 323
See application file for complete search history.

(56) References Cited

U.S. PATENT DOCUMENTS

| | | | | |
|---|---|---|---|---|
| 3,280,145 | A | 10/1966 | Hofmann | |
| 5,242,925 | A * | 9/1993 | Boettcher et al. | 514/254.06 |
| 5,418,237 | A | 5/1995 | Bottcher et al. | |
| 5,532,241 | A * | 7/1996 | Bottcher et al. | 514/254.09 |
| 5,670,511 | A * | 9/1997 | Marz et al. | 514/290 |
| 5,693,655 | A * | 12/1997 | Bottcher et al. | 514/323 |
| 5,698,553 | A * | 12/1997 | Prucher et al. | 514/222.8 |
| 5,726,177 | A * | 3/1998 | Halazy et al. | 514/254.09 |
| 6,197,773 | B1 | 3/2001 | Howard et al. | |
| 6,251,908 | B1 * | 6/2001 | Bottcher et al. | 514/254.09 |
| 6,255,306 | B1 * | 7/2001 | Macor | 514/253.09 |
| 6,323,229 | B1 | 11/2001 | Howard et al. | |
| 6,399,616 | B1 * | 6/2002 | Peglion et al. | 514/253.04 |
| 6,451,803 | B1 | 9/2002 | Howard | |
| 6,486,171 | B2 * | 11/2002 | Peglion et al. | 514/300 |
| 6,723,725 | B1 * | 4/2004 | Bottcher et al. | 514/254.09 |
| 6,838,461 | B1 * | 1/2005 | Boettcher et al. | 514/254.09 |
| 6,844,362 | B2 | 1/2005 | Brown et al. | |
| 6,900,212 | B1 * | 5/2005 | Bartoszyk et al. | 514/254.09 |
| 7,138,527 | B2 | 11/2006 | Brown et al. | |
| 7,183,294 | B2 | 2/2007 | Brown et al. | |
| 7,220,763 | B2 * | 5/2007 | Chakravarty et al. | 514/359 |
| 2004/0014768 | A1 * | 1/2004 | Gottschlich et al. | 514/253.06 |

FOREIGN PATENT DOCUMENTS

| | | | |
|---|---|---|---|
| EP | 0496222 | | 7/1992 |
| EP | 0 709 384 | | 5/1996 |
| EP | 0709384 | | 5/1996 |
| EP | 0 952 154 | | 10/1999 |
| EP | 0952154 | | 10/1999 |
| EP | 1078928 | A1 * | 2/2001 |
| EP | 1 440 966 | | 7/2004 |
| EP | 1 460 064 | | 9/2004 |
| FR | 1344579 | | 11/1962 |
| FR | 0 496 222 | | 7/1992 |
| WO | WO 96/03400 | | 2/1996 |
| WO | WO 9603400 | | 2/1996 |

OTHER PUBLICATIONS

Beilstein Datenbank, Beilstein Registry Nummern (BRN) 121327, 395771, 395821, 3540022, 3541195, 3542111, 6329287, 6329720, 6644293, 7812825, 7814418, 7827556, 8764267, 8765991, 8767774. 2009.
Beilstein Datenbank, Beilstein Registry Nummern (BRN) 4802458, 140357. 2009.

* cited by examiner

*Primary Examiner*—Rei-tsang Shiao
(74) *Attorney, Agent, or Firm*—Millen, White, Zelano, Branigan, P.C.

(57) ABSTRACT

Substituted indoles of the formula (I) and physiologically acceptable derivatives and salts thereof, in which $R^1$, D, E, $R^{12}$, p, $X^1$, E, G, $X^2$ and Z are as defined in claim 1, exhibit particular actions on the central nervous system, especially 5HT reuptake-inhibiting and 5 HTx-agonistic and/or -antagonistic actions and in particular serotonin-agonistic and -antagonistic properties and can be employed as antipsychotics, neuroleptics, antidepressants, anxiolytics and/or antihypertonics. They can furthermore be employed as excitatory amino acid antagonists for combating neurodegenerative diseases, including cerebrovascular diseases, epilepsy, schizophrenia, Alzheimer's disease, Parkinson's disease, Huntington's disease, cerebral ischaemia, infarction or psychoses.

(I)

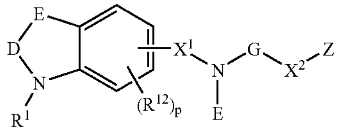

7 Claims, No Drawings

SUBSTITUTED INDOLES

This application is a 371 of PCT/EP03/03806 filed on Apr. 11, 2003.

The invention relates to substituted indoles of the formula I

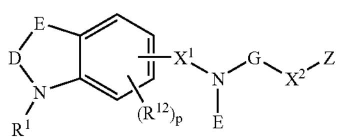

I in which $R^1$ is H, A or $SO_2A$,

A is straight-chain or branched alkyl having from 1 to 10 carbon atoms, alkenyl having from 2 to 10 carbon atoms or alkoxy-alkyl having from 2 to 10 carbon atoms, and D-E is $R^2C{=}CR^4$ or $R^2R^3C{—}CR^4R^5$, in which $R^2$, $R^3$, $R^4$ and $R^5$ are selected, independently, from H, A, cycloalkyl having from 3 to 7 carbon atoms, Hal, $CH_2Hal$, $CH(Hal)_2$, $C(Hal)_3$, $NO_2$, $(CH_2)_nCN$, $(CH_2)_n N(R^6)_2$, $(CH_2)_nN(R^6)Ar$, $(CH_2)_nN(R^6)Het$, $(CH_2)_nN(Ar)_2$, $(CH_2)_nN(Het)_2$, $(CH_2)_nCOOR^6$, $(CH_2)_nCOOAr$, $(CH_2)_nCOOHet$, $(CH_2)_nCON(R^6)_2$, $(CH_2)_nCON(R^6)Ar$, $(CH_2)_nCON(R^6)Het$, $(CH_2)_nCON(Ar)_2$, $(CH_2)_nCON(Het)_2$, $(CH_2)_nNR^6COR^6$, $(CH_2)_nNR^6CON(R^6)_2$, $(CH_2)_nNR^6SO_2A$, $(CH_2)_nSO_2N(R^6)_2$, $(CH_2)_nSO_2N\ R^6(CH_2)_mAr$, $(CH_2)_nSO_2NR^6(CH_2)_mHet$, $(CH_2)_nS(O)_wR^6$, $(CH_2)_nS(O)_wAr$, $(CH_2)_nS(O)_wHet$, $(CH_2)_nOOCR^6$, $(CH_2)_nHet$, $(CH_2)_nAr$, $(CH_2)_nCOR^6$, $(CH_2)_nCO(CH_2)_mAr$, $(CH_2)_nCO(CH_2)_mHet$, $(CH_2)_nCOO(CH_2)_mAr$, $(CH_2)_n COO(CH_2)_mHet$, $(CH_2)_nOR^6$, $(CH_2)_nO(CH_2)_m Ar$, $(CH_2)_nO(CH_2)_mHet$, $(CH_2)_nSR^6$, $(CH_2)_nS(CH_2)_mAr$, $(CH_2)_nS(CH_2)_mHet$, $(CH_2)_nN(R^6)(CH_2)_m Ar$, $(CH_2)_nN(R^6)(CH_2)_mHet$, $(CH_2)_nSO_2N(R^6)(CH_2)_mAr$, $(CH_2)_nN(R^6)SO_2(CH_2)_mAr$, $(CH_2)_nSO_2N(R^6)(CH_2)_mHet$, $(CH_2)_nN(R^6)S_2(CH_2)_mHet$, $(CH_2)_nCON(R^6)(CH_2)_mAr$, $(CH_2)_nN(R^6)CO(CH_2)_mAr$, $(CH_2)_nCON(R^6)(CH_2)_mHet$, $(CH_2)_nN(R^6CO(CH_2)_mHet$, $CH{=}N{—}OA$, $CH_2CH{=}N{—}OA$, $(CH_2)_n NHOA$, $(CH_2)_nCH{=}N\text{-}Het$, $(CH_2)_nOCOR^6$, $(CH_2)_nOC(O)N(R^6)_2$, $(CH_2)_nOC(O)NR^6(CH_2)_mAr$, $(CH_2)_nOC(O)NR^6(CH_2)_mHet$, $(CH_2)_nNR^6COOR^6$, $(CH_2)_nNR^6COO(CH_2)_mAr$, $(CH_2)_nNR^6COO(CH_2)_mHet$, $(CH_2)_nN(R^6)CH_2CH_2OR^6$, $(CH_2){=}N(R^6)CH_2CH_2OCF_3$, $(CH_2)_nN(R^6)C(R^6)HCOOR^6$, $(CH_2)_n N(R^6)CH_2COHet$, $(CH_2)_nN(R^6)CH_2Het$, $(CH_2)_nN(R^6)CH_2H_2N(R^6)CH_2COOR^6$, $(CH_2)_nN(R^6)CH_2CH_2N(R^6)_2$, $CH{=}CHCOOR^6$, $CH{=}CHCH_2NR^6$ Het, $CH{=}CHCH_2N(R^6)_2$, $CH{=}CHCH_2OR^6$, $(CH_2)_nN(COOR^6)COOR^6$, $(CH_2)_nN(CONH_2)COOR^6$, $(CH_2)_nN(CONH_2)CONH_2$, $(CH_2)_nN(CH_2COOR^6)COOR^6$, $(CH_2)_nN(CH_2CONH_2)COOR^6$, $(CH_2)_nN(CH_2CONH_2)CONH_2$, $(CH_2)_nCHR^6COR^6$, $(CH_2)_nCHR^6COOR^6$, $(CH_2)_nCHR^6CH_2R^6$, $(CH_2)_nOCN$ or $(CH_2)_nNCO$, in which $R^6$ is selected, independently, from H, A or cycloalkyl having from 3 to 7 carbon atoms, Het is a saturated, unsaturated or aromatic mono- or bicyclic heterocyclic radical which is unsubstituted or mono- or poly-substituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2N(R^6)_2$, $S(O)_wA$ and/or $OOCR^6$, Ar is an aromatic hydrocarbon radical having from 6 to 14 carbon atoms which is unsubstituted or mono- or polysubstituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2N(R^6)_2$, $S(O)_wA$ and/or $OOCR^6$, w is 0, 1, 2 or 3, and n and m, independently of one another, are 0, 1, 2, 3, 4 or 5;

$X^1$ is $(CHR^7)_g$ or $(CHR^7)_h\text{-}Q\text{-}(CHR^8)_k$, in which

Q is selected from O, S, $N{—}R^6$, $(O{—}CHR^7)_g$, $(CHR^7{—}O)_g$, $CR^9{=}CR^{10}$, $(O{—}CHR^9CHR^{10})_g$, $(CHR^9CHR^{10}{—}O)_g$, $C{=}O$, $C{=}S$, $C{=}NR^6$, $CH(OR^6)$, $C(OR^6)(OR^6)$, $C({=}O)O$, $OC({=}O)$, $OC({=}O)O$, $C({=}O)N(R^6)$, $N(R^6)C({=}O)$, $C({=}S)N(R^6)$, $N(R^6)C({=}S)$, $OC({=}O)N(R^6)$, $N(R^6)C({=}O)O$, $CH{=}N{—}O$, $CH{=}N{—}NR^6$, $OC(O)NR^6$, $NR^6C(O)O$, $S{=}O$, $SO_2$, $SO_2NR^6$ and $NR^6SO_2$, g is 1, 2, 3, 4, 5 or 6, h and k, independently of one another, are 0, 1, 2, 3, 4, 5 or 6, and $R^7$, $R^8$, $R^9$, $R^{10}$ and $R^{12}$ are selected, independently, from the meanings indicated for $R^2$ to $R^5$;

p is 0, 1, 2 or 3

E is H, A, $(CH_2)_nHet$, $(CH_2)_nAr$ or cycloalkyl having from 3 to 7 carbon atoms, G is an optionally substituted alkylene radical having from 1 to 4 carbon atoms, where the substituents are selected from the meanings indicated for $R^4$, or E and G, together with the N atom to which they are bonded, are an unsubstituted or substituted 5-, 6- or 7-membered, mono- or bicyclic heterocyclic radical, which may have 1, 2 or 3 further heteroatoms selected from N, O and S, $X^2$ is a bond or is selected, independently, from the meanings indicated for $X^1$, Z is H or is a saturated, mono- or polyethylenically unsaturated or aromatic carbocyclic radical having from 5 to 10 carbon atoms or a saturated, mono- or polyethylenically unsaturated or aromatic heterocyclic radical having from 4 to 9 carbon atoms, where the carbocyclic or heterocyclic radical may be mono- or polysubstituted, where the substituents are selected, independently of one another, from the meanings of $R^2$ to $R^5$ other than H, and where the heterocyclic radical contains from 1 to 4 heteroatoms selected, independently of one another, from N, O and S, and Hal is F, Cl, Br or I, and salts and solvates thereof, preferably physiologically tolerated salts and solvates thereof and in particular physiologically tolerated salts thereof.

Benzylpiperidine derivatives with high affinity to binding sites of amino acid receptors are disclosed, for example, in EP 0 709 384 A1.

The invention had the object of finding novel compounds having valuable properties, in particular those which have an improved action profile, for example higher activity, higher selectivity or a broader use profile and/or less severe side effects. It should preferably be possible to prepare the novel compounds simply and inexpensively, and they should be, in particular, suitable for the preparation of medicaments.

Surprisingly, it has been found that the object is achieved by the compounds of the formula I. In particular, it has been found that the compounds of the formula I and salts thereof have very valuable pharmacological properties as well as being well tolerated.

The compounds according to the invention exhibit particular actions on the central nervous system, especially 5HT reuptake-inhibiting and $5HT_x$-agonistic and/or -antagonistic actions, where $HT_x$ is preferably taken to mean $HT_{1A}$, $HT_{1D}$, $HT_{2A}$ and/or $HT_{2C}$.

Since the compounds inhibit serotonin reuptake, they are particularly suitable as antipsychotics, neuroleptics, antidepressants, anxiolytics and/or antihypertonics. The compounds exhibit serotonin-agonistic and -antagonistic properties. They inhibit the binding of tritiated serotonin ligands to hippocampal receptors (Cossery et al., European J. Pharmacol. 140 (1987), 143-155) and synaptosomal serotonin reuptake (Sherman et al., Life Sci. 23 (1978), 1863-1870). In addition, changes in DOPA accumulation in the striatum and 5-HT accumulation in various regions of the brain occur (Seyfried et al., European J. Pharmacol. 160 (1989), 31-41). The $5\text{-}HT_{1A}$-antagonistic action is detected in vitro, for example, by inhibition of the abolition of electrically induced contraction of the guinea pig ileum caused by 8-OH-DPAT (Fozard and Kilbinger, Br. J. Pharmacol. 86 (1985) 601P). The $5\text{-}HT_{1A}$-antagonistic action is detected ex vivo by inhibition of 5-HTP accumulation reduced by 8-OH-DPAT (Seyfried et al., European J. Pharmacol. 160 (1989), 31-41) and the antagonisation of 8-OH-DPAT-induced effects in the ultrasound vocalisation test (DeVry, Psych-pharmacol. 121 (1995), 1-26). Inhibition of serotonin reuptake can be detected ex vivo using synaptosomal uptake inhibition (Wong et al., Neuropsychopharmacol. 8 (1993), 23-33) and p-chloroamphetamine antagonism (Fuller et al., J. Pharmacol. Exp. Ther. 212 (1980), 115-119). Furthermore, analgesic and hypotensive actions occur.

The compounds are therefore suitable for the treatment of schizophrenia, cognitive deficits, anxiety, depression, nausea, tardive dyskinesia, gastrointestinal tract disorders, learning disorders, age-related memory disorders, psychoses and for positively influencing obsessive-compulsive disorder (OCD) and eating disorders (for example bulimia). They exhibit actions on the central nervous system, in particular additional $5\text{-}HT_{1A}$-agonistic and 5-HT reuptake-inhibiting actions. They are likewise suitable for the prophylaxis of and combating the consequences of cerebral infarction (apoplexia cerebri), such as strokes and cerebral ischaemia, and for the treatment of extrapyramidal motor side effects of neuroleptics and of Parkinson's disease.

The compounds of the formula I are therefore suitable both in veterinary and in human medicine for the treatment of dysfunctions of the central nervous system and of inflammation. They can be used for the prophylaxis of and for combating the consequences of cerebral infarction (apoplexia cerebri), such as strokes and cerebral ischaemia, and for the treatment of extrapyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord trauma. However, they are also suitable as medicament active ingredients for anxiolytics, antidepressants, antipsychotics, neuroleptics, antihypertonics and/or for positively influencing obsessive-compulsive disorder, sleeping disorders, tardive dyskinesia, learning disorders, age-related memory disorders, eating disorders, such as bulimia, and/or sexual dysfunctions.

The compounds according to the invention particularly preferably exhibit high bioavailability and/or are capable of significantly increasing the serotonin level in the brain.

The present invention therefore relates to compounds according to the invention as medicament or medicament active ingredient.

The present invention therefore relates to the use of the compounds according to the invention for the preparation of a medicament for the prophylaxis and/or therapy of diseases in which 5HT plays a role.

These diseases are preferably selected from depression, strokes, cerebral ischaemia, extrapyramidal motor side effects of neuroleptics and of Parkinson's disease, Alzheimer's disease, amyotrophic lateral sclerosis, brain and spinal cord trauma, obsessive-compulsive disorder, sleeping disorders, tardive dyskinesia, learning disorders, age-related memory disorders, eating disorders, such as bulimia, and/or sexual dysfunctions.

Furthermore, the compounds according to the invention preferably exhibit particularly high affinity to binding sites of amino acid receptors, in particular to the ifenprodil binding site on the NMDA receptor (NMDA=N-methyl D-aspartate), which allosterically modulates the polyamine binding site.

The binding test for $[^3H]$-ifenprodil can be carried out by the method of Schoemaker et al., Eur. J. Pharmacol. 176, 249-250 (1990).

The compounds are suitable for the treatment of neurodegenerative diseases, including cerebrovascular diseases. The novel compounds can likewise be used as analgesicsor anxiolytic and for the treatment of epilepsy, schizophrenia, Alzheimer's disease, Parkinson's disease, Huntington's disease, cerebral ischaemia or infarction. They are furthermore suitable for the treatment of psychoses caused by excessively high amino acid levels.

The $[^3H]$-CGP-39653 binding test for the glutamate binding site of the NMDA receptor can be carried out, for example, by the method of M. A. Stills et al., described in Eur. J. Pharmacol. 192, 19-24 (1991). The test for the glycine binding site of the NMDA receptor can be carried out by the method of M. B. Baron et al., described in Eur. J. Pharmacol. 206, 149-154 (1991).

The action against Parkinson's disease, i.e. potentiation of the L-DOPA-induced contralateral rotation in hemiparkinsonian rats, can be demonstrated by the method of U. Ungerstedt and G. W. Arbuthnott, Brain Res. 24, 485 (1970).

The compound is particularly suitable for the treatment or prophylaxis of strokes and for protection against and for the treatment of cerebral oedema and states of undersupply of the central nervous system, in particular hypoxia or anoxia.

The said effects can in addition be demonstrated or checked by the methods as described in the following references: J. W. McDonald, F. S. Silverstein and M. V. Johnston, Eur. J. Pharmacol. 140, 359 (1987); R. Gill, A. C. Foster and G. N. Woodruff, J. Neurosci. 7, 3343 (1987); J. B. Bederson et al., Stroke, 17, 472-476 (1986); S. Brint et al., J. Cereb. Blood Flow Metab. 8, 474-485 (1988).

The references listed below disclose various antagonists which are able to block various binding sites of the NMDA receptor: W. Danysz, C. G. Parsons, I. Bresink and G. Quack, Drug, News & Perspectives 8, 261 (1995), K. R. Gee, Exp. Opin. Invest. Drugs 3, 1021 (1994) and J. J. Kulagowski and L. L. Iversen, J. Med. Chem. 37, 4053 (1994).

Ifenprodil and eliprodil of the formulae IV and V respectively are able to block the NMDA receptor by interacting with the modulatory polyamine binding site (C. J. Carter, K. G. Lloyd, B. Zivkovic and B. Scatton, J. Pharmacol. Exp. Ther. 253, 475 (1990)).

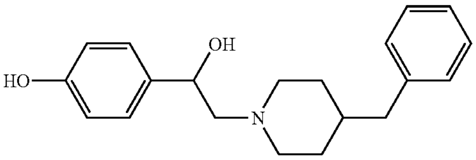

IV

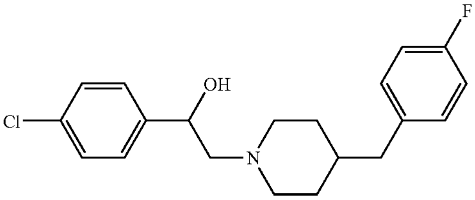

V

Since ifenprodil and eliprodil interact with the polyamine binding site on the NMDA receptor, the antagonistic activity of the compounds according to the invention can be determined in a spermine-stimulated [$^3$H]MK-801 (dizocilpine) binding test.

In the presence of saturation concentrations of glycine and NMDA, spermine is able further to increase the binding of MK-801, which is inhibited by ifenprodil, eliprodil and very particularly effectively by the compounds according to the invention.

In addition, the compounds according to the invention can be tested in a [$^3$H]GABA (γ-aminobutyric acid) liberation test, analogously to J. Dreijer, T. Honoré and A. Schousboe, J. Neurosci. 7, 2910 (1987), which, as an in-vitro model, describes the antagonistic function in the cell.

The invention accordingly relates to the compounds of the formula I according to claim 1 and/or physiologically acceptable salts thereof as antagonists to receptors of excitatory amino acids, such as, for example, glutamic acid, and salts thereof.

The invention relates to the compounds of the formula I according to claim 1 and physiologically acceptable salts and solvates thereof as glycine transporter inhibitor.

In particular, the invention relates to the compounds of the formula I according to claim 1 and/or acceptable salts thereof as excitatory amino acid antagonists for combating neurodegenerative diseases, including cerebrovascular diseases, epilepsy, schizophrenia, Alzheimer's disease, Parkinson's disease, Huntington's disease, cerebral ischaemia, infarction or psychoses.

The invention also relates to the use of the compounds of the formula I according to claim 1 and/or physiologically acceptable salts thereof for the preparation of a medicament for combating neurodegenerative diseases, including cerebrovascular diseases, epilepsy, schizophrenia, Alzheimer's disease, Parkinson's disease, Huntington's disease, cerebral ischaemia, infarction or psychoses.

The compounds of the formula I can be employed as medicament active ingredient in human and veterinary medicine.

The invention furthermore relates to a process for the preparation of the compounds of the formula I according to claim 1 and physiologically acceptable salts thereof, characterised in that a) a compound of the formula II

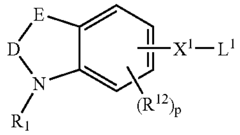

II in which $L^1$ is Cl, Br, I, OH, a reactively esterified OH group or a diazonium group, and $R^1$, D, E, $R^{12}$, p and $X^1$ are as defined above and below for the compounds of the formula I, b) is reacted with a compound of the formula III

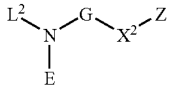

III in which $L^2$ is H or a metal ion, and E, G, $x^2$ and Z are as defined above and below for the compounds of the formula I, and optionally d) the resultant compound of the formula I is converted into one of its salts by treatment with an acid.

In a preferred embodiment, the compound of the formula III is selected from compounds of the formula

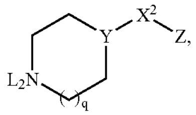

in which $L^2$, q, y, $X^2$ and Z are as defined above and below.

The compound of the formula VI is particularly preferably selected from compounds of the formulae

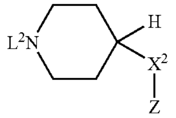

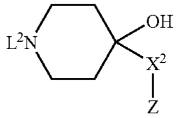

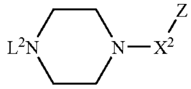

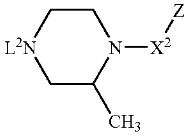

and

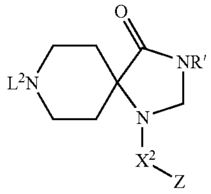

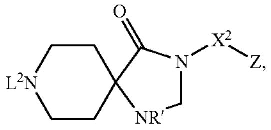

or the thioamides thereof, in which $L^2$, $X^2$ and Z are as defined above and below, and R' is H, A, $(CH_2)_n$Het, $(CH_2)_n$Ar, cycloalkyl having from 3 to 7 carbon atoms or $SO_2A$.

The process according to the invention can be carried out as a one-pot reaction, i.e. isolation and/or purification steps are omitted as far as possible and only the desired end product, i.e. generally a compound according to the invention or a pharmaceutically usable derivative thereof, is purified and/or isolated. Alternatively, a purification and/or isolation step can be carried out after each of the said reaction steps. Mixed forms of the procedures described above are also conceivable. Suitable purification and isolation steps are known to the person skilled in the art, for example from Houben-Weyl, Methoden der organischen Chemie [Methods of Organic Chemistry], Georg-Thieme-Verlag, Stuttgart.

In particular, the invention relates to the compounds of the formula I in which at least one of the said radicals has one of the preferred meanings indicated above.

For the purposes of the present invention, alkyl is a linear or branched alkyl radical, preferably an unbranched alkyl radical, which has 1, 2, 3, 4, 5, 6, 7, 8, 9 or 10 carbon atoms, preferably 1, 2, 3, 4 or 5 carbon atoms, and may be mono- or polysubstituted by halogen (Hal), for example perfluorinated. If an alkyl radical is substituted by halogen, it preferably, depending on the number of carbon atoms of the alkyl radical, has 1, 2, 3, 4 or 5 halogen atoms. Thus, for example, a methyl group (alkyl radical having 1 carbon atom) can be mono-, di- or trisubstituted by halogen, and an ethyl group (alkyl radical having 2 carbon atoms) can be mono-, di-, tri-, tetra- or pentasubstituted by halogen.

For alkyl groups having more than 2 carbon atoms, the same preferably applies as for ethyl groups. Alkyl is particularly preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or hexyl.

The term "alkenyl" preferably covers mono- or polyethylenically unsaturated, straight-chain or branched hydrocarbon radicals having from 2 to 10 and in particular from 3 to 6 carbon atoms, and in particular allyl, 2- or 3-butenyl, isobutenyl, sec-butenyl, furthermore preferably 4-pentenyl, isopentenyl or 5-hexenyl.

The term "alkoxy" is preferably a radical of the formula —O-alkyl, in which alkyl is as defined above, or, if two alkoxy radicals are bonded to adjacent (vicinal) carbon atoms, "alkoxy" is preferably —O-alkylene-O—, in which alkylene is as defined above. Preferred alkoxy radicals of the formula —O-alkyl are methoxy, ethoxy and propoxy. Preferred alkoxy radicals of the formula —O-alkylene-O— are $—O—CH_2—O—$, $—O—CH_2CH_2—O—$ and $—O—CH_2CH_2CH_2—O—$.

The term "alkoxyalkyl" preferably covers straight-chain radicals of the formula $C_uH_{2u+1}—O—(CH_2)_v$, in which u and v are each, independently of one another, from 1 to 6. Particularly preferably, u=1 and v=1 to 4.

The term "aryl" preferably covers an unsubstituted or mono- or polysubstituted benzene ring, for example an unsubstituted or substituted phenyl radical or an unsubstituted or mono- or polysubstituted system of benzene rings, such as, for example, anthracene, phenanthrene or naphthalene ring systems. Examples of suitable substituents include alkyl, alkoxy, oxo, hydroxyl, mercapto, amino, nitro, cyano and halogen radicals.

The term "aryl" preferably covers an unsubstituted or mono- or polysubstituted aromatic ring system, for example an unsubstituted or substituted phenyl radical or an unsubstituted or mono- or polysubstituted system of benzene rings, such as, for example, anthracene, phenanthrene or naphthalene ring systems. Examples of suitable substituents include alkyl, alkoxy, oxo, hydroxyl, mercapto, amino, nitro, cyano and halogen radicals.

The term "aralkyl" preferably covers an aryl radical as defined above bonded to an alkyl radical as defined above. Examples of suitable aralkyl radicals include, but are not restricted to, benzyl, phenylpropyl, phenylbutyl and the like.

Ar is preferably an aryl radical which is unsubstituted or mono- or polysubstituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$ and/or $OOCR^6$, and in particular phenyl, naphthyl or biphenyl, each of which is unsubstituted or substituted as above.

Het is preferably a saturated, unsaturated or aromatic mono- or bicyclic heterocyclic radical which is unsubstituted or mono- or polysubstituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$ and/or $OOCR^6$. Het is preferably a radical which is unsubstituted or substituted as described above, selected from 1-piperidyl, 1-piperazyl, 1-(4-methyl)piperazyl, 4-methylpiperazin-1-ylamine, 4-morpholinyl, 1-pyrrolidinyl, 1-pyrazolidinyl, 1-(2-methyl)pyrazolidinyl, 1-imidazolidinyl or 1-(3-methyl)imidazolidinyl, thiophen-2-yl or thiophen-3-yl, 2-, 3- or 4-pyridyl, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl.

The radical Z is preferably a 5- or 6-membered, polyethylenically unsaturated or aromatic carbocyclic radical, which may be mono- or polysubstituted, preferably mono- to trisubstituted, where the substituents are selected, independently of one another, from the meanings of $R^4$ other than H, or are preferably selected from A, in particular alkyl having from 1 to 6 carbon atoms, alkoxy having from 1 to 6 carbon atoms and alkoxyalkyl having from 2 to 6 carbon atoms, Hal, in particular F and Cl, $NO_2$, $OR^6$, $N(R^6)_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and C(NH)NOH. Examples of carbocyclic radicals Q are cyclopentadienyl, cyclohexadienyl, phenyl, naphthyl, in particular 1-naphthyl and 2-naphthyl, and biphenyl, each of which may be substituted as described above/below. The carbocyclic radical Z is preferably phenyl and particularly preferably substituted phenyl, in particular 4-alkylphenyl, such as 4-tolyl (4-methylphenyl), 4-alkoxyphenyl, such as 4-methoxyphenyl, 3,4-dialkoxyphenyl, such as 3,4-dimethoxyphenyl and 3,4-methylenedioxyphenyl, and 4-halophenyl, such as 4-fluorophenyl and 4-chlorophenyl.

The radical Z is alternatively preferably a 5- or 6-membered, polyethylenically unsaturated or aromatic heterocyclic radical, which may contain from 1 to 4 heteroatoms, selected, independently of one another, from N, O and S, and may be mono- or polysubstituted, preferably mono- to trisubstituted, where the substituents are selected, independently of one another, from the meanings of $R^4$ other than H, or are preferably selected from A, in particular alkyl having from 1 to 6 carbon atoms, alkoxy having from 1 to 6 carbon atoms and alkoxyalkyl having from 2 to 6 carbon atoms, Hal, in particular F and $C_1$, $NO_2$, $OR^6$, $N(R^6)_2$, CN, $COOR^6$, $CON(R^6)_2$, $NR^6COR^6$, $NR^6CON(R^6)_2$, $NR^6SO_2A$, $COR_1$, $SO_2NR^6$, $S(O)_wA$, $OOCR^6$ and C(NH)NOH. Examples of heterocyclic radicals Q are furanyl, thiophenyl, pyrrolyl, imidazolyl, pyrazolyl, triazolyl, tetrazolyl, thiazolyl, oxazolyl, isoxazolyl, oxadiazolyl, oxopyridyl, thiadiazolyl, isothiazolyl, pyridyl, pyridazyl, pyrazinyl, pyrimidyl, quinolinyl, isoquinolinyl, benzofuranyl, benzothiophenyl, benzo[1,4]dioxoinyl, 2,3-dihydrobenzo[1,4]dioxinyl, benzothiadiazolyl, chromenyl, 2-oxochromenyl, indolyl and indazolyl, each of which may be substituted as described above/below. The heterocyclic radical Z is particularly preferably optionally substituted furanyl, thiophenyl, pyrrolyl, pyridyl, pyridazyl, pyrazolyl, pyrazinyl, pyrimidyl, benzofuranyl, 2-oxochromenyl indolyl, benzothiadiazolyl, quinolinyl, 2,3-dihydrobenzo[1,4]dioxinyl and benzo[d]isothiazolyl.

The present invention preferably relates to compounds of the formula I as described above in which $R^1$, p, E, G and Z have the meanings given above and below and in which A is straight-chain alkyl having from 1 to 4 carbon atoms or branched alkyl having from 3 to 6 carbon atoms, and D-E is $R^2C{=}CR^4$ or $R^2R^3C{-}CR^4R^5$, in particular $R^2C{=}CR^4$, in which $R^2$, $R^3$ and $R^5$ are selected, independently, from H, A and cycloalkyl having from 3 to 7 carbon atoms, and $R^4$ is Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$, $(CH_2)_nNR^6COR^6$, $(CH_2)_nNR^6CON(R^6)_2$, $(CH_2)_n NR^6SO_2A$, $(CH_2)_nSO_2N(R^6)_2$, $(CH_2)_nS(O)_wA$, $(CH_2)_nOOCR^6$, $(CH_2)_nCOR^6$, $(CH_2)_nCO(CH_2)_mAr$, $(CH_2)_nCO(CH_2)_mHet$, $(CH_2)_nCOO(CH_2)_mAr$, $(CH_2)_n COO(CH_2)_mHet$, $(CH_2)_nOR^6$, $(CH_2)_nO(CH_2)_mAr$, $(CH_2)_nO(CH_2)_mHet$, $(CH_2)_nSR^6$, $(CH_2)_nS(CH_2)_mAr$, $(CH_2)_nS(CH_2)_mHet$, $(CH_2)_nN(R^6)(CH_2)_mAr$, $(CH_2)_nN(R^6)(CH_2)_mHet$, $(CH_2)_nSO_2N(R^6)(CH_2)_mAr$, $(CH_2)_nN(R^6)SO_2(CH_2)_mAr$, $(CH_2)_nSO_2N(R^6)(CH_2)_mHet$, $(CH_2)_nN(R^6)S_2(CH_2)_mHet$, $(CH_2)_nCON(R^6)(CH_2)_m Ar$, $(CH_2)_nN(R^6)CO(CH_2)_mAr$, $(CH_2)_nCON(R^6)(CH_2)_m$ Het, $(CH_2)_nN(R^6)CO(CH_2)_mHet$, $(CH_2)_nN(R^6)_2$, $(CH_2)_nOCOR^6$, $(CH_2)_nOC(O)N(R^6)_2$, $(CH_2)_nC(O)NR^6(CH_2)_mAr$, $(CH_2)_nOC(O)NR^6(CH_2)_mHet$, $(CH_2)_nNR^6COOR^6$, $(CH_2)_nNR^6COO(CH_2)_mAr$, $(CH_2)_n$ $NR^6COO(CH_2)_mHet$, $(CH_2)_nN(R^6)CH_2CH_2OR^6$, $(CH_2)_nN(R^6)CH_2CH_2OCF_3$, $(CH_2)_nN(R^6)C(R^6)HCOOR^6$, $(CH_2)_nN(R^6)CH_2COHet$, $(CH_2)_nN(R^6)CH_2Het$, $(CH_2)_nN(R^6)CH_2CH_2N(R^6)CH_2COOR^6$, $(CH_2)_nN(R^6)CH_2CH_2N(R^6)_2$, $CH{=}CHCOOR^6$, $(CH_2)_nN(COOR^6)COOR^6$, $(CH_2)_nN(CONH_2)COOR^6$, $(CH_2)_nN(CONH_2)CONH_2$, $(CH_2)_nN(CH_2COOR^6)COOR^6$, $(CH_2)_nN(CH_2CONH_2)COOR^6$, $(CH_2)_nN(CH_2CONH_2)CONH_2$, $(CH_2)_nCHR^6COR^6$, $(CH_2)_nCHR^6COOR^6$ or $(CH_2)_nCHR^6CH_2OR^6$ and in particular Hal, $CH_2Hal$, $CH(Hal)_2$, $C(Hal)_3$, $NO_2$, $(CH_2)_nCN$, $(CH_2)_nCOOR^6$ $(CH_2)_n CON(R^6)_2$, $(CH_2)_nSO_2N(R^6)_2$ or $(CH_2)_nS(O)_w A$, m is 0, 1, 2, 3, 4 or 5 and n is 0, 1, 2 or 3 and in particular 0 or 1;

$X^1$ is $(CHR^7)_g$ or $Q\text{-}(CHR^8)_k$, in which

Q is selected from O, S, $N{-}R^6$, $(O{-}CHR^7)_g$, $(CHR^7{-}O)_g$, $CR^9{=}CR^{10}$, $(O{-}CHR^9CHR^{10})_g$, $(CHR^9CHR^{10}{-}O)_g$, C=O, C=S, $C{=}NR^6$, $C(OR^6)(OR^6)$, C(=O)O, OC(=O), OC(=O)O, $C(=O)N(R^6)$, $N(R^6)C(=O)$, $OC(=O)N(R^6)$, $N(R^6)C(=O)O$, CH=N—O, $CH{=}N{-}NR^6$, $OC(O)NR^6$, $NR^6C(O)O$, S=O, $SO_2$, $SO_2NR^6$ and $NR^6SO_2$, g is 1, 2, 3, 4, 5 or 6 and in particular 2, 3 or 4, k is 0, 1, 2, 3, 4, 5 or 6 and in particular 1, 2 or 3, and $R^7$, $R^8$, $R^9$ and $R^{10}$ are selected, independently, from the meanings indicated for $R^2$ to $R^5$;

$X^2$ is a bond or independently is $(CHR^7)_g$ or $Q\text{-}(CHR^8)_k$, in which Q is selected from O, S, $N{-}R^6$, $(O{-}CHR^7)_g$, $(CHR^7{-}O)_g$, $(O{-}CHR^9CHR^{10})_g$, $(CHR^9CHR^{10}{-}O)_g$, C=O, $CH(OR^6)$, C(=O)O, OC(=O), $C(=O)N(R^6)$, $N(R^6)C(=O)$, S=O, $SO_2$, $SO_2NR^6$ and $NR^6SO_2$, where g in $X^2$ is preferably 1 or 2 and k in $X^2$ is preferably 0 or 1, and $R^{12}$ is selected, independently, from the meanings of $R^4$ other than H and in particular, independently, is F, Cl, Br, I, CN, $NO_2$, $NH_2$, $CF_3$, $OCF_3$, C(NH)NOH or $SO_2CH_3$, and solvates and salts thereof.

The invention preferably relates to substituted indoles of the formula Ia.

Ia

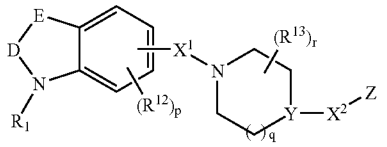

in which $R^1$, D-E and Z are as defined above, and in which $X^1$ is $(CHR^7)_g$ or $(CHR^7)_h\text{-}Q\text{-}(CHR^8)_k$, in which Q is selected from O, S, $N{-}R^6$, $(O{-}CHR^7)_g$, $(CHR^7{-}O)_g$, $CR^9{=}CR^{10}$, $(O{-}CHR^9CHR^{10})_g$, $(CHR^9CHR^{10}{-}O)_g$, C=O, C=S, $C{=}NR^6$, $CH(OR^6)$, $C(OR^6)(OR^6)$, C(=O)O, OC(=O), OC(=O)O, $C(=O)N(R^6)$, $N(R^6)C(=O)$, $OC(=O)N(R^6)$, $N(R^6)C(=O)O$, CH=N—O, $CH{=}N{-}NR^6$, $OC(O)NR^6$, $NR^6C(O)O$, S=O, $SO_2$, $SO_2NR^6$ and $NR^6SO_2$, g is 1, 2, 3, 4, 5 or 6, h and k, independently of one another, are 0, 1, 2, 3, 4, 5 or 6, and $R^6$ is selected, independently, from H, A or cycloalkyl having from 3 to 7 carbon atoms, $R^7$, $R^8$, $R^9$ and $R^{10}$ are selected, independently, from the meanings indicated for $R^2$ to $R^5$;

Y is CH, N, $COR^{11}$, $CSR^{11}$, an unsubstituted or substituted, spiro-linked carbocyclic radical having from 5 to 7 carbon atoms or an unsubstituted or substituted, spiro-linked, 5-, 6- or 7-membered heterocyclic radical having from 1 to 3 heteroatoms selected from N, S or O, $R^{11}$ is H, A, $(CH_2)_nHet$, $(CH_2)_nAr$ or cycloalkyl having from 3 to 7 carbon atoms, $X^2$ is a bond or is selected, independently, from the meanings indicated for $X^1$, and is preferably a bond or O, S, $N{-}R^7$, $CH_2$ or $CH_2CH_2$, p, q and r, independently of one another, are 0, 1, 2 or 3 and Hal is F, Cl, Br or I, and $R^{12}$ and $R^{13}$, independently of one another, are selected from the meanings of $R^4$ other than H and are preferably, independently of one another, Hal, CN, $NO_2$, $OR^6$, $N(R^6)_2$, $NO_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and/or C(NH)NOH, and salts and solvates thereof, preferably physiologically tolerated salts and solvates thereof and in particular physiologically tolerated salts thereof.

The sum of n and m is preferably greater than zero.

In the compounds of the formula I, the E-N-G-$X^2$-Z group is preferably selected from groups of the formulae

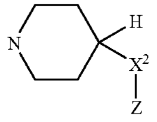
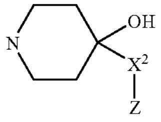

-continued

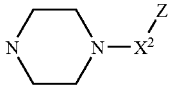 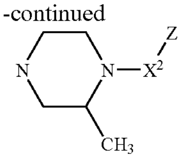 and

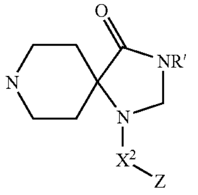 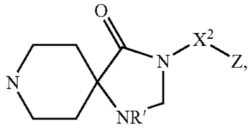

or the thioamides thereof, in which $X^2$ and Z are as defined above and below, and R' is H, A, $(CH_2)_n$Het, $(CH_2)_n$Ar, cycloalkyl having from 3 to 7 carbon atoms or $SO_2$A.

In the compounds of the formula I, of the formula Ia and the compounds of the formula III, the $X^2$-Z group is preferably selected from the groups

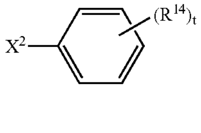 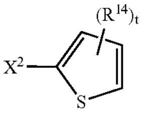 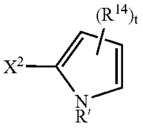

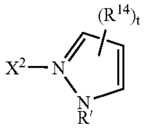 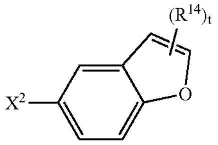

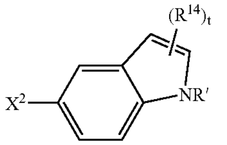 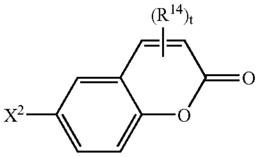

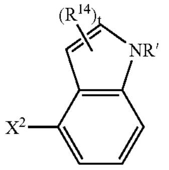 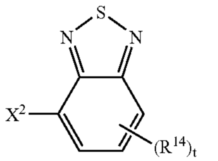

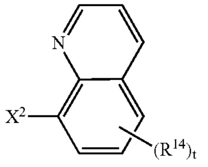 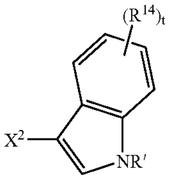

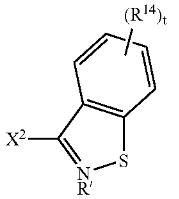 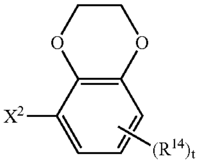

in which $R^{14}$ is selected, independently, from Hal, A, $(CH_2)_n$Het, $(CH_2)_n$Ar, $(CH_2)_n COO(CH_2)_m$Ar, $(CH_2)_n COO(CH_2)_m$ Het, $(CH_2)_n OR^6$, $(CH_2)_n O(CH_2)_m$Ar, $(CH_2)_n O(CH_2)_m$ Het, $(CH_2)_n N(R^6)(CH_2)_m$Ar, $(CH_2)_n N(R^6)(CH_2)_m$Het, $(CH_2)_n SO_2N(R^6)(CH_2)_m$Ar, $(CH_2)_n N(R^6)SO_2(CH_2)_m$ Ar, $(CH_2)_n SO_2N(R^6)(CH_2)_m$Het, $(CH_2)_n N(R^6)SO_2$ $(CH_2)_m$Het, $(CH_2)_n N(R^6)_2$, $(CH_2)_n$NHOA, $(CH_2)_n(R^6)$ Het, $(CH_2)_n OCOR^6$, $(CH_2)_n OC(O)N(R^6)_2$, $(CH_2)_n$OC (O)$NR^6(CH_2)_m$Ar, $(CH_2)_n OC(O)NR^6(CH_2)_m$Het, $(CH_2)_n NR^6COOR^6$, $(CH_2)_n NR^6COO(CH_2)_m$Ar, $(CH_2)_n NR^6COO(CH_2)_m$Het, and in particular, independently of one another, is Hal, $NO_2$, $OR^6$, $N(R^6)_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_w$A, $OOCR^6$ and/or C(NH)NOH, W is 0, 1, 2 or 3, t is 0, 1, 2, 3, 4 or 5 and in particular 0, 1, 2 or 3, and R' is H, A, $(CH_2)_n$Het, $(CH_2)_n$Ar, cycloalkyl having from 3 to 7 carbon atoms or $SO_2$A.

If the $X^2$-Z group is the

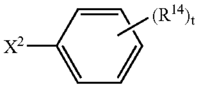

group, it is preferably selected from the groups

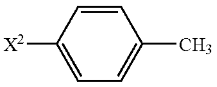 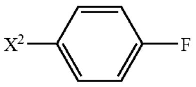

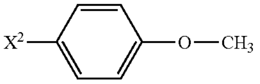

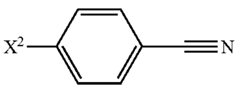 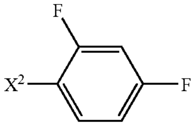

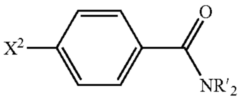

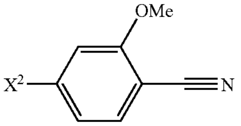

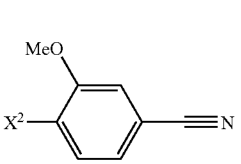 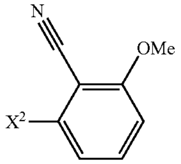

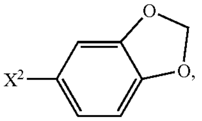

in which $X^2$ and R' are as defined above/below.

In a preferred embodiment of the present invention, n is 0 or 1 and in particular 0.

In a particularly preferred embodiment of the present invention, n in the radicals $R^2$, $R^3$, $R^4$ and/or $R^5$, preferably in the radicals $R^2$ and/or $R^4$ and in particular in the radical $R^4$ is 0.

Some preferred groups of compounds can be expressed by the following sub-formulae Ia) to In), which conform to the formula I and/or to the formula Ia and in which the radicals not designated in greater detail have the meaning indicated above/below, but in which in Ia) $R^1$ is H or $SO_2A$ and in particular H or $SO_2$—$CH_3$;

in Ib) $R^1$ is H or $SO_2A$ and in particular H or $SO_2$—$CH_3$;
D-E is is $R^2C$═$CR^4$;

in Ic) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$, in Id) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;

in Ie) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A;

in If) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A, and
n is 0 or 1;

in Ig) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A,
n is 0 or 1,
$X^1$ is $(CHR^7)_g$, in which g is 2, 3 or 4, or is
Q-$(CHR^8)_k$, in which k is 1, 2 or 3;

in Ih) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A,
n is 0 or 1,
$X^1$ is $(CHR^7)_g$, in which g is 2, 3 or 4, or is
Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$;

in Ii) $R^1$ is H or $SO_2A$ and in particular H or $SO_2$—$CH_3$;
D-E is is $R^2C$═$CR^4$;
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A,
n is 0 or 1,
$X^1$ is $(CHR^7)_g$, in which g is 2, 3 or 4, or is
Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$, and
$R^7$ and $R^8$ are selected, independently of one another, from H and A;

in Ij) $R^1$ is H or $SO_2A$ and in particular H or $SO_2$—$CH_3$;
D-E is is $R^2C$═$CR^4$,
$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;
$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and
$R^6$ is H or A,
n is 0 or 1,
$X^1$ is $(CHR^7)_g$, in which g is 2, 3 or 4, or is
Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$,
$R^7$ and $R^8$ are selected, independently of one another, from H and A, and Y is CH, $COR^{11}$, N or an unsubstituted or substituted, spiro-linked, 5-, 6- or 7-membered heterocyclic radical having from 1 to 3 heteroatoms selected from N, S or O, in Ik) $R^1$ is H or $SO_2A$ and in particular H or $SO_2$—$CH_3$;

D-E is is $R^2C$═$CR^4$;

$R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;

$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and $R^6$ is H or A, n is 0 or 1, $X^1$ is $(CHR^7)_g$, in which g is 2, 3 or 4, or is Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$, $R^7$ and $R^8$ are selected, independently of one another, from H and A, Y is CH, $COR^{11}$, N or an unsubstituted or substituted, spiro-linked, 5-, 6- or 7-membered heterocyclic radical having from 1 to 3 heteroatoms selected from N, S or O; and $R^{11}$ is H or A;

in Il) $R^1$ is H or $SO_2A$ and in particular H or $SO_2$—$CH_3$;

D-E is is $R^2C$═$CR^4$, $R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;

$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and $R^6$ is H or A, n is 0 or 1, $X^1$ is $(CHR^7)_g$, in which g is 2, 3 or 4, or is Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$, $R^7$ and $R^8$ are selected, independently of one another, from H and A, Y is CH, $COR^{11}$, N or an unsubstituted or substituted, spiro-linked, 5-, 6- or 7-membered heterocyclic radical having from 1 to 3 heteroatoms selected from N, S or O, $R^{11}$ is H or A, and $X^2$ is $CH_2$, $CH_2CH_2$, HCOH, O, S, N—$R^6$, $CONR^6$, C═O or a bond;

in Im) $R^1$ is H or $SO_2A$ and in particular H or $SO_2$—$CH_3$;

D-E is is $R^2C$═$CR^4$, $R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;

$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and $R^6$ is H or A, n is 0 or 1, $X^1$ is $(CHR^7)_g$, in which g is 2, 3 or 4, or is Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$, $R^7$ and $R^8$ are selected, independently of one another, from H and A, Y is CH, $COR^{11}$, N or an unsubstituted or substituted, spiro-linked, 5-, 6- or 7-membered heterocyclic radical having from 1 to 3 heteroatoms selected from N, S or O, $R^{11}$ is H or A, and $X^2$ is $CH_2$, $CH_2CH_2$, HCOH, O, S, N—$R^6$, $CONR^6$, C═O or a bond, and $R^{12}$ is selected, independently, from A, Hal, CN, $NO_2$, $OR^6$, $N(R^6)_2$, $COOR^6$, $CON(R^6)_2$, $COR^6$, $SO_2N(R^6)_2$ and $S(O)_wA$;

in In) $R^1$ is H or $SO_2A$ and in particular H or $SO_2$—$CH_3$;

D-E is is $R^2C$═$CR^4$, $R^2$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$;

$R^4$ is H, alkyl having from 1 to 3 carbon atoms, alkoxyalkyl having from 2 to 5 carbon atoms, Hal, $CH_2Hal$, $CH(Hal)_2$, $C(Hal)_3$, $NO_2$, $(CH_2)_nCN$, $(CH_2)_nCOOR^6$, $(CH_2)_nCON(R^6)_2$ $(CH_2)_nSO_2N(R^6)_2$ or $(CH_2)_nS(O)_wR^6$ and $R^6$ is H or A, n is 0 or 1, $X^1$ is $(CHR^7)_g$, in which g is 2, 3 or 4, or is Q-$(CHR^8)_k$, in which k is 1, 2 or 3 and Q is selected from O, S, N—$R^6$, $CONR^6$, C═O, C═S, S═O, $SO_2$, $SO_2NR^6$ and $NR^6SO_2$, $R^7$ and $R^8$ are selected, independently of one another, from H and A, Y is CH, $COR^{11}$, N or an unsubstituted or substituted, spiro-linked, 5-, 6- or 7-membered heterocyclic radical having from 1 to 3 heteroatoms selected from N, S or O, $R^{11}$ is H or A, and $X^2$ is $CH_2$, $CH_2CH_2$, HCOH, O, S, N—$R^6$, $CONR^6$, C═O or a bond, and $R^{12}$ is selected, independently, from A, Hal, CN, $NO_2$, $OR^6$, $N(R^6)_2$, $COOR^6$, $CON(R^6)_2$, $COR^6$, $SO_2N(R^6)_2$ and $S(O)_wA$, and $R^{14}$ is selected, independently, from A, Hal, CN, $NO_2$, $OR^6$, $N(R^6)_2$, $COOR^6$, $CON(R^6)_2$, $COR^6$, $SO_2N(R^6)_2$ and $S(O)_wA$.

In a preferred embodiment of the present invention, the radical $R^2$ in the sub-formulae Ia) to In) is H, A, in particular alkyl having from 1 to 4 carbon atoms or O-alkyl having from 1 to 4 carbon atoms, Hal, in particular F or Br, CN, $NO_2$ $NH_2$, $CF_3$, $OCF_3$ $SO_2CH_3$, $COOR^6$ or $CON(R^6)_2$, particularly preferably H, alkyl having from 1 to 4 carbon atoms or CN; and $R^4$ is H, A, in particular alkyl having from 1 to 4 carbon atoms or O-alkyl having from 1 to 4 carbon atoms, Hal, in particular F or Br, CN, $NO_2$ $NH_2$, $CF_3$, $OCF_3$ $SO_2CH_3$, $COOR^6$ or CON $(R^6)_2$, particularly preferably CN. In this preferred embodiment, $R^2$ is H or A in particular if $R^4$ is Hal, $NO_2$ $NH_2$, $CF_3$, $OCF_3$ $SO_2CH_3$, $COOR^6$ or $CON(R^6)_2$ and in particular is CN. In this preferred embodiment, the compound of the formula I and/or of the formula Ia preferably has one or two substituents $R^{12}$ and particularly preferably no substituents $R^{12}$. In this preferred embodiment, the compound of the formula I and/or of the formula Ia particularly preferably has one or two substituents $R^{13}$ and very particularly preferably no substituents $R^{13}$. In this preferred embodiment, the compound of the formula I and/or of the formula Ia preferably has no, one or two substituents $R^{14}$ and in particular one or two substituents $R^{14}$. If the compound of the formula I and/or of the formula Ia has one or two substituents $R^{14}$, these are preferably selected from F, Cl, Br, I, CN, $CF_3$ and $OCF_3$ and in particular are selected from F, $CF_3$ and $OCF_3$.

In a specific and preferred embodiment, the present invention relates to a compound of the formula I and/or of the formula Ia and in particular a compound of the sub-formulae Ia) to In) in which D-E is $R^2C{=}CR^4$, $R^2$ is H or methyl and $R^4$ is CN, and solvates and salts thereof.

In a further specific and preferred embodiment, the present invention relates to a compound of the formula I and/or of the formula Ia and in particular a compound of the sub-formulae Ia) to In) in which $X^1$ is $CH_2CH_2$ (i.e. is $(CHR^7)_g$ in which $R^7$ is H and g is 2), $CH_2CH_2CH_2$ (i.e. is $(CHR^7)_9$ in which $R^7$ is H and g is 3) or $OCH_2CH_2$ (i.e. is $(CHR^7)_h$-Q-$(CHR^8)_k$ in which h is 0, $R^8$ is H and k is 2), and solvates and salts thereof.

In a further specific and preferred embodiment, the present invention relates to a compound of the formula I and/or of the formula Ia and in particular a compound of the sub-formulae Ia) to In) in which Y is CH, CHOH (i.e. is $COR^{11}$ in which $R^{11}$ is H) or N and in particular is CH, and solvates and salts thereof.

In a further specific and preferred embodiment, the present invention relates to a compound of the formula I and/or of the formula Ia and in particular a compound of the sub-formulae Ia) to In) in which Y is an unsubstituted or substituted, spiro-linked, 5-, 6- or 7-membered heterocyclic radical having from 1 to 3 heteroatoms selected from N, S or O, and particularly preferably an unsubstituted or substituted, spiro-linked, 5-membered heterocyclic radical having 2 heteroatoms, preferably 2 N atoms. In this embodiment, the spiro-linked heterocyclic radical preferably has, as one substituent, a double-bonded oxygen radical (=O), i.e. an oxo substituent, or a double-bonded sulfur radical (=S), i.e. a thioxo substituent. The spiro-linked heterocyclic radical particularly preferably has, as one substituent, an oxo substituent. The spiro-linked heterocyclic radical is very particularly preferably selected from structures of the formulae

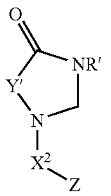 and 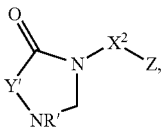

in which $X^2$, Z and R' are as defined above/below, and Y' is the spiro-linking carbon atom of the spiro-linked heterocyclic radical. In this embodiment, $X^2$ is particularly preferably a bond. In particular, the spiro-linked heterocyclic radical is therefore selected from structures of the formulae

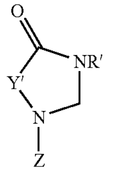 and 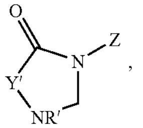, in which $X^2$, Z and R' are as defined above/below, and Y' is the spiro-linking carbon atom of the spiro-linked heterocyclic radical.

In a further specific and preferred embodiment, the present invention relates to a compound of the formula I and/or of the formula Ia and in particular a compound of the sub-formulae Ia) to In) in which $X^2$ is $CH_2$ (i.e. is $(CHR^7)_g$ in which $R^7$ is H and g is 1), $CH_2CH_2$ (i.e. is $(CHR^7)_g$ in which $R^7$ is H and g is 2), $OCH_2$ (i.e. is $(CHR^7)_h$-Q-$(CHR^8)_k$ in which Q is O, h is O, $R^8$ is H and k is 1), O (i.e. is $(CHR^7)_h$-Q-$(CHR^8)_k$ in which Q is 0 and h and k are 0), S (i.e. is $(CHR^7)_h$-Q-$(CHR^8)_k$ in which Q is S and h and k are 0), C=O (i.e. is $(CHR^7)_h$-Q-$(CHR^8)_k$ in which Q is C=O and h and k are 0), or NH (i.e. is $(CHR^7)_h$-Q-$(CHR^8)_k$ in which Q is N—$R^6$, $R^6$ is H and h and k are 0), particularly preferably is $CH_2$, O, NH and CHOH and in particular is $CH_2$ or O, and solvates and salts thereof.

In a further specific and preferred embodiment, the present invention relates to a compound of the formula I and/or of the formula Ia and in particular a compound of the sub-formulae Ia) to In) in which $x^2$ is a chemical bond between the groups Y and Z. In this embodiment, the Y—$X^2$-Z group is thus the Y-Z group.

In a further specific and preferred embodiment, the E-N-G-$X^2$-Z group in the compounds of the formula I is a radical of the formula

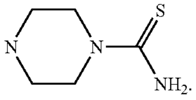

In a further specific and preferred embodiment, the E-N-G-$X^2$-Z group in the compounds of the formula I is a radical of the formula

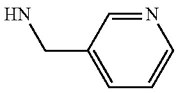, 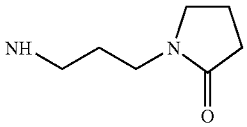

or a radical of the formula

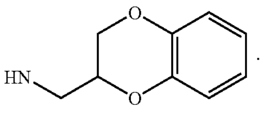

In a further specific and preferred embodiment, the E-N-G-$X^2$-Z group in the compounds of the formula I is a radical of the formula

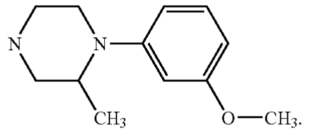

In a particularly preferred embodiment, the present invention relates to a compound of the formula I and/or of the formula Ia and in particular a compound of the sub-formulae Ia) to In) which comprises the features of one or more of the embodiments described above and in particular the features of all embodiments described above or the features of all embodiments described above which are not mutually exclusive.

In the compounds of the formula I and/or of the formula Ia, $X^1$ is, relative to the indole nitrogen, preferably in the 4-, 5- or 6-position, particularly preferably the 4-position or 6-position and in particular in the 4-position of the indole radical (in accordance with IUPAC nomenclature for indole systems).

In the compounds of the formula I and/or of the formula Ia, the substituents $R^{14}$ are preferably in the ortho- and/or para-position, relative to Z.

The present invention therefore particularly preferably relates to compounds of the formulae Iα, Iβ and Iχ

Iα

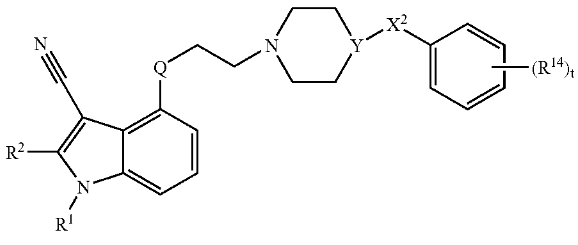

Iβ

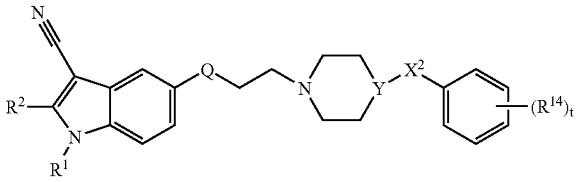

Iχ

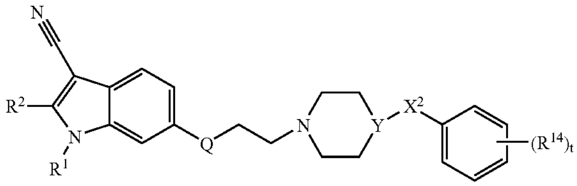

in which $R^1$, $R^2$, Q, Y, $X^2$, $R^{14}$ and t are as defined above and in particular in the above sub-formulae Ia) to In) and/or the above embodiments, and compounds of the formulae Iδ, Iε and Iζ

Iδ

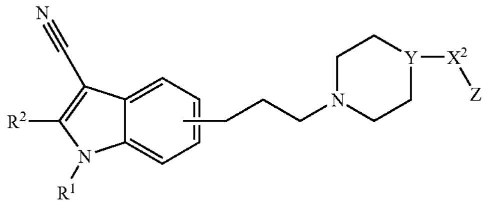

Iε

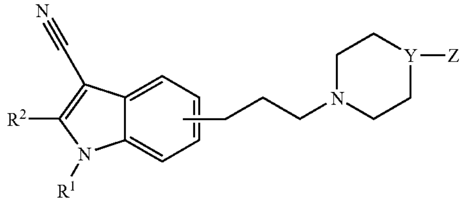

Iζ

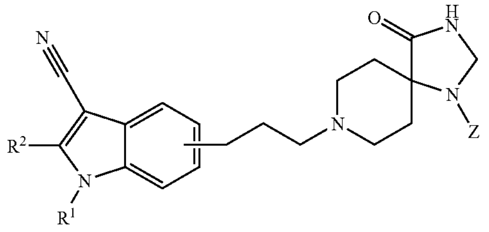

in which $R^1$, $R^2$, Y, $X^2$ and Z are as defined above and in particular in the above sub-formulae Ia) to In) and/or the above embodiments.

In the compounds of the formulae Iα, Iβ and Iχ, $(R^{14})_t$ is particularly preferably a fluorine substituent in the para-position, two fluorine substituents, one of which is in the para-position and one is in the meta-position, relative to Z, or $CONH_2$ in the para-position. Furthermore, in the formulae Iα, Iβ and Iχ, $R^1$ and/or $R^2$ are preferably H, Q is $CH_2$ and Y is CH and $X^2$ is O or $CH_2$.

In the compounds of the formulae Iδ and Iε, the group Y is particularly preferably N or CH. In the compounds of the formula Iζ, the group Z is particularly preferably substituted and in particular unsubstituted phenyl.

In the compounds of the formula Iδ, the group Y—$X^2$-Z is preferably a radical of the formula

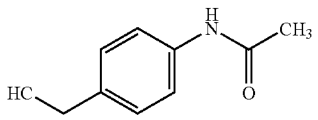

or a radical of the formula

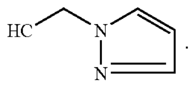

In the compounds of the formula Iε, the group Y-Z is particularly preferably a radical of the formulae

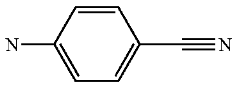
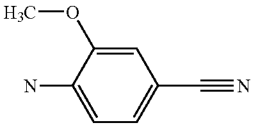
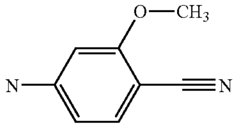
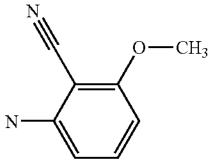
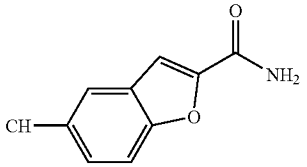
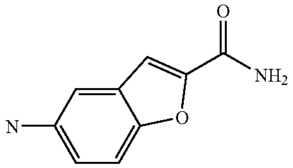
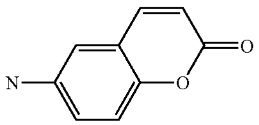
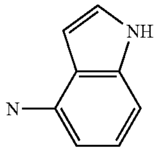
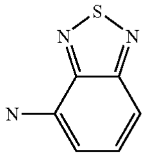
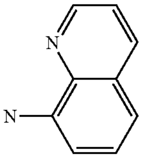
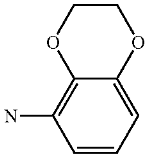
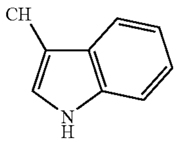
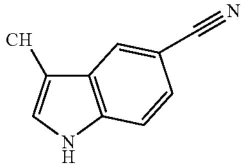
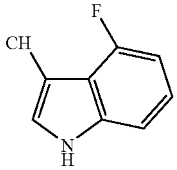
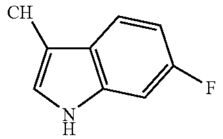
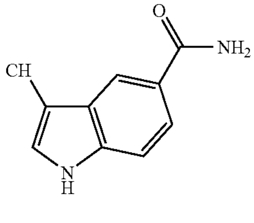
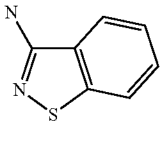
or a radical of the formulae
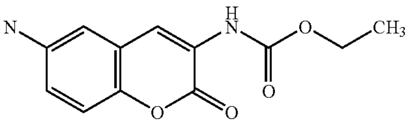
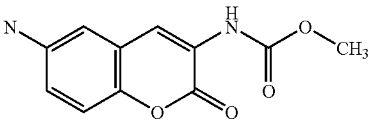
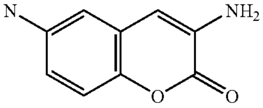
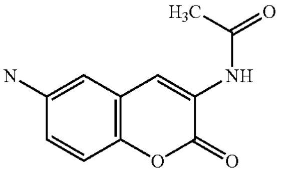
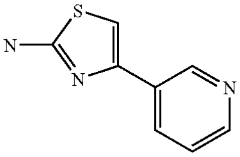
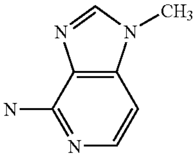
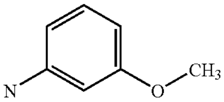
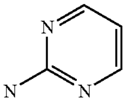
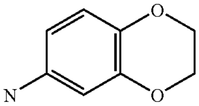
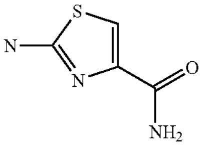
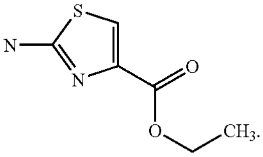
In a very particularly preferred embodiment of the present invention, the compounds of the formula I and/or of the formula Ia are selected from
a)
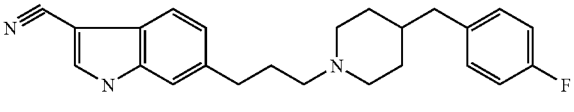

6-{3-[4-(4-Fluorobenzyl)-1-piperidyl]propyl}-1H-indole-3-carbonitrile;

b)

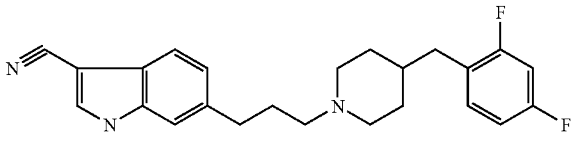

6-{3-[4-(2,4-Difluorobenzyl)-1-piperidyl]propyl}-1H-indole-3-carbonitrile;

c)

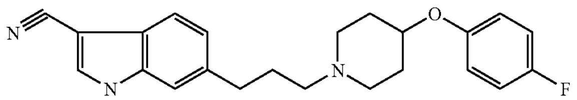

6-{3-[4-(4-Fluorophenoxy)-1-piperidyl]propyl}-1H-indole-3-carbonitrile;

d)

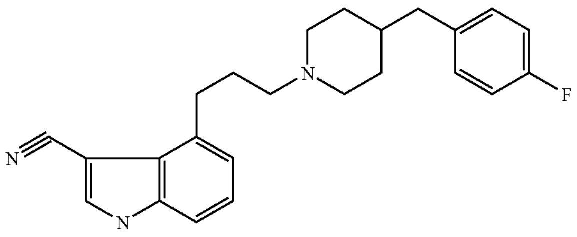

4-{3-[4-(4-Fluorobenzyl)-1-piperidyl]propyl}-1H-indole-3-carbonitrile;

e)

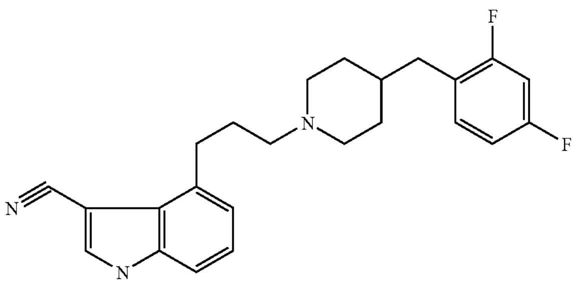

4-{3-[4-(2,4-Difluorobenzyl)-1-piperidyl]propyl}-1H-indole-3-carbonitrile;

f)

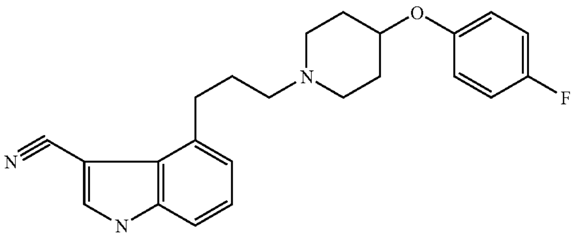

4-{3-[4-(4-Fluorophenoxy)-1-piperidyl]propyl}-1H-indole-3-carbonitrile;

g)

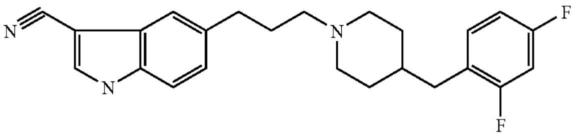

5-{3-[4-(2,4-Difluorobenzyl)-1-piperidyl]propyl}-1H-indole-3-carbonitrile;

h)

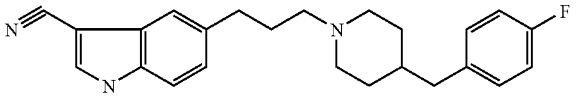

5-{3-[4-(4-Fluorobenzyl)-1-piperidyl]propyl}-1H-indole-3-carbonitrile;

i)

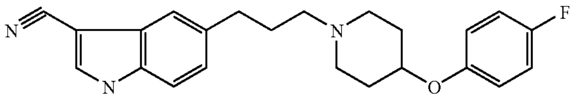

5-{3-[4-(4-Fluorophenoxy)-1-piperidyl]propyl}-1H-indole-3-carbonitrile;

j)

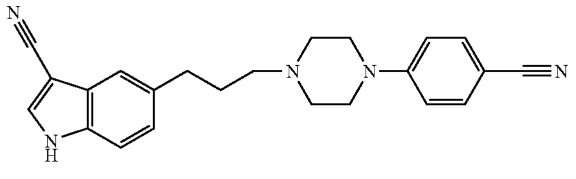

5-{3-[4-(4-Cyanophenyl)piperazin-1-yl]propyl}-1H-indole-3-carbonitrile k)

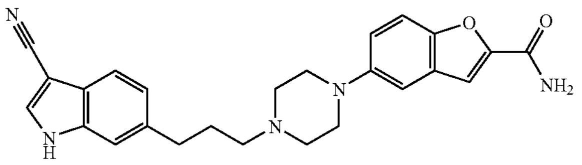

5-{4-[3-(3-Cyano-1H-indol-6-yl)propyl]piperazin-1-yl}benzofuran-2-carboxamide l)

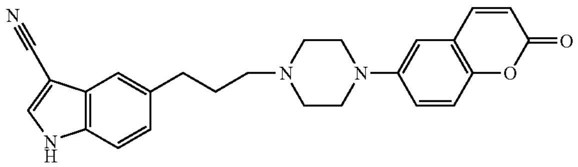

5-{3-[4-(2-Oxo-2H-chromen-6-yl)piperazin-1-yl]propyl}-1H-indole-3-carbonitrile m)

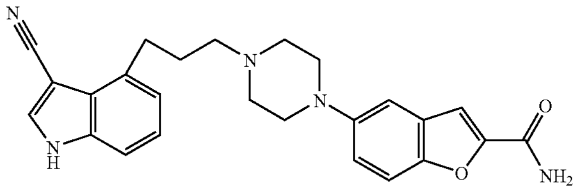

5-{4-[3-(3-Cyano-1H-indol-4-yl)propyl]piperazin-1-yl}benzofuran-2-carboxamide n)

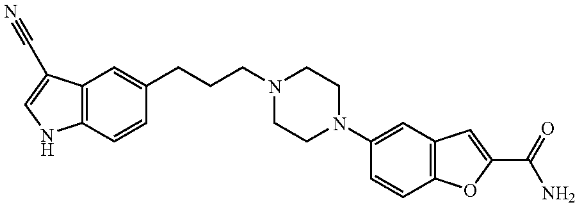

5-{4-[3-(3-Cyano-1H-indol-5-yl)propyl]piperazin-1-yl}benzofuran-2-carboxamide o)

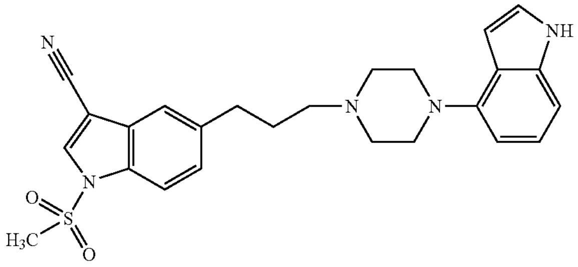

5-{3-[4-(1H-indol-4-yl)piperazin-1-yl]propyl}-1-methanesulfonyl-1H-indole-3-carbonitrile p)

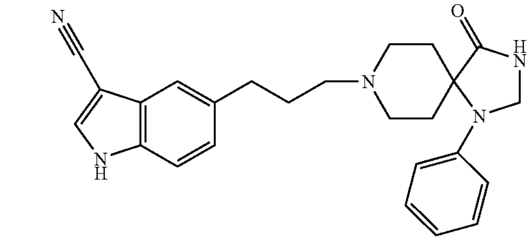

5-[3-(4-Oxo-1-phenyl-1,3,8-triazaspiro[4.5]dec-8-yl)propyl]-1H-indole-3-carbonitrile q)

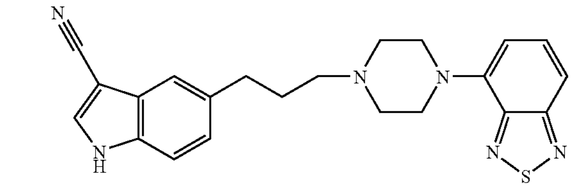

5-[3-(4-Benzo[1,2,5]thiadiazol-4-ylpiperazin-1-yl)propyl]-1H-indole-3-carbonitrile r)

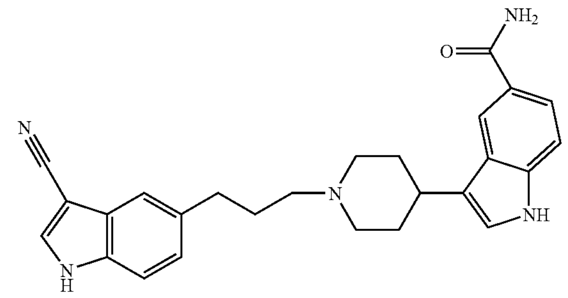

3-{1-[3-(3-Cyano-1H-indol-5-yl)propyl]piperidin-4-yl}-1H-indole-5-carboxamide s)

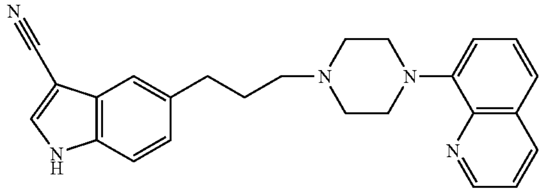

5-[3-(4-Quinolin-8-ylpiperazin-1-yl)propyl]-1H-indole-3-carbonitrile t)

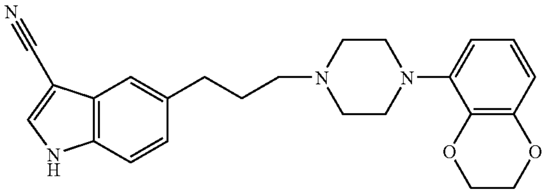

5-{3-[4-(2,3-Dihydrobenzo[1,4]dioxin-5-yl)piperazin-1-yl]propyl}-1H-indole-3-carbonitrile u)

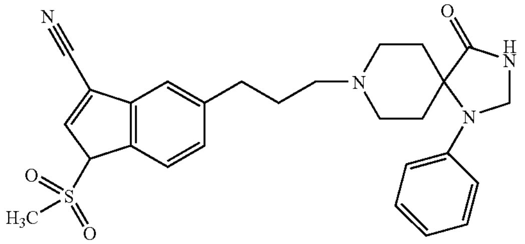

1-Methanesulfonyl-5-[3-(4-oxo-1-phenyl-1,3,8-triazaspiro[4.5]dec-8-yl)propyl]-1H-indole-3-carbonitrile v)

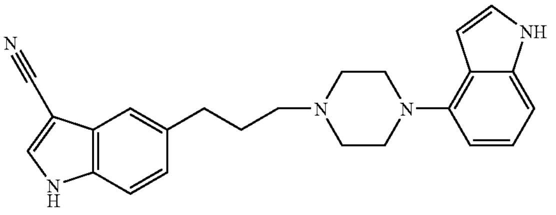

5-{3-[4-(1H-indol-4-yl)piperazin-1-yl]propyl}-1H-indole-3-carbonitrile w)

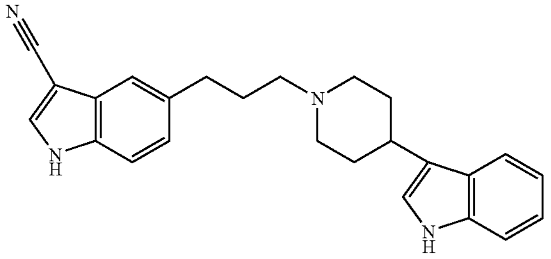

5-{3-[4-(1H-indol-3-yl)piperidin-1-yl]propyl}-1H-indole-3-carbonitrile x)

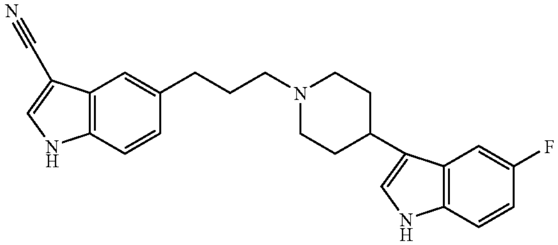

5-{3-[4-(5-Fluoro-1H-indol-3-yl)piperidin-1-yl]propyl}-1H-indole-3-carbonitrile y)

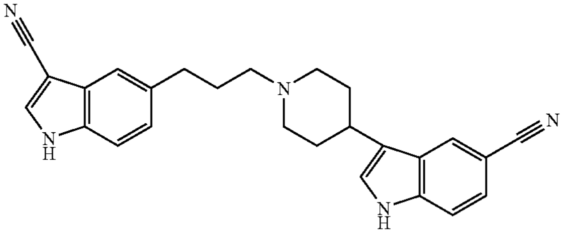

3-{1-[3-(3-Cyano-1H-indol-5-yl)propyl]piperidin-4-yl}-1H-indole-5-carbonitrile z)

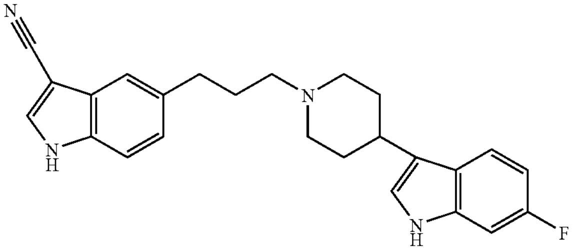

5-{3-[4-(6-Fluoro-1H-indol-3-yl)piperidin-1-yl]propyl}-1H-indole-3-carbonitrile aa)

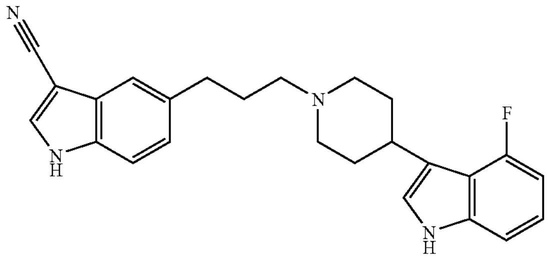

5-{3-[4-(4-Fluoro-1H-indol-3-yl)piperidin-1-yl]propyl}-1H-indole-3-carbonitrile bb)

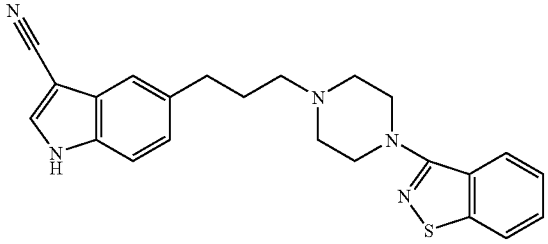

5-[3-(4-Benzo[d]isothiazol-3-ylpiperazin-1-yl)propyl]-1H-indole-3-carbonitrile cc)

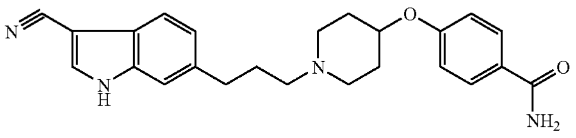

4-{1-[3-(3-Cyano-1H-indol-6-yl)propyl]piperidin-4-yloxy}benzamide dd)

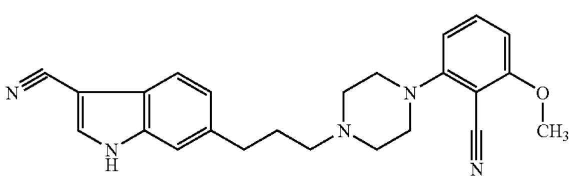

6-{3-[4-(2-Cyano-3-methoxyphenyl)piperazin-1-yl]propyl}-1H-indole-3-carbonitrile ee)

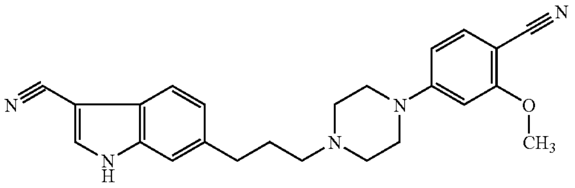

6-{3-[4-(4-Cyano-3-methoxyphenyl)piperazin-1-yl]propyl}-1H-indole-3-carbonitrile (ff)

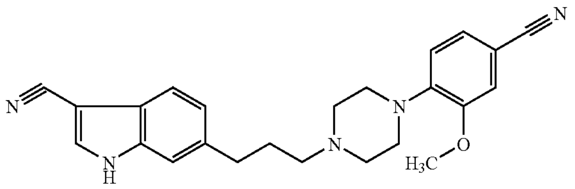

6-{3-[4-(4-Cyano-2-methoxyphenyl)piperazin-1-yl]propyl}-1H-indole-3-carbonitrile gg)

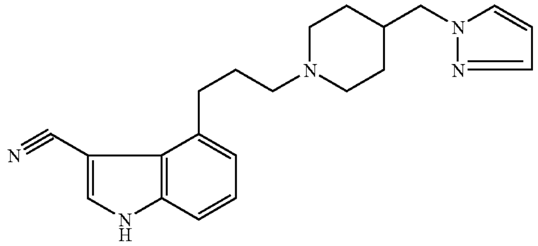

4-[3-(4-Pyrazol-1-ylmethyl-1-piperidyl)propyl]-1H-indole-3-carbonitrile hh)

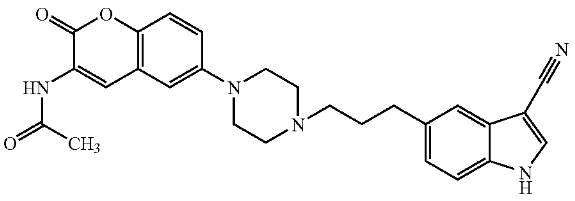

N-(6-{4-[3-(3-Cyano-1H-indol-5-yl)propyl]piperazin-1-yl}-2-oxo-2H-chromen-3-yl)acetamide ii)

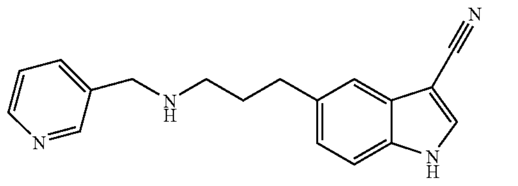

5-{3-[(Pyridin-3-ylmethyl)amino]propyl}-1H-indole-3-carbonitrile jj)

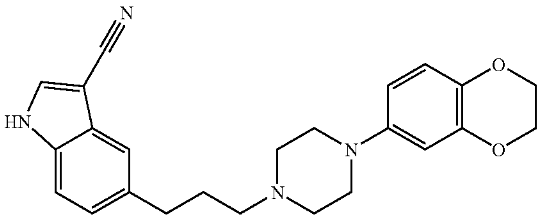

5-{3-[4-(2,3-Dihydrobenzo[1,4]dioxin-6-yl)piperazin-1-yl]propyl}-1H-indole-3-carbonitrile kk)

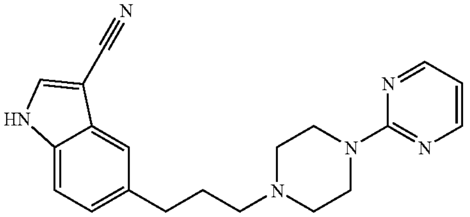

5-[3-(4-Pyrimidin-2-ylpiperazin-1-yl)propyl]-1H-indole-3-carbonitrile ll)

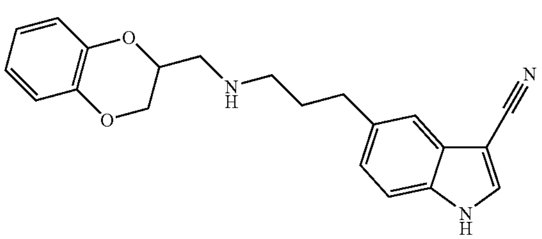

5-{3-[(2,3-Dihydrobenzo[1,4]dioxin-2-ylmethyl)amino]propyl}-1H-indole-3-carbonitrile mm)

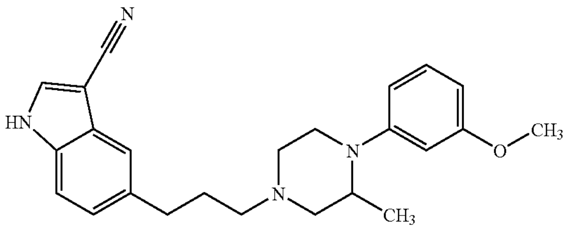

5-{3-[4-(3-Methoxyphenyl)-3-methylpiperazin-1-yl]propyl}-1H-indole-3-carbonitrile nn)

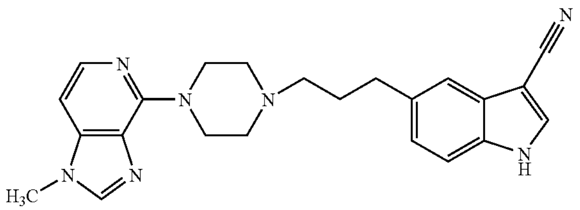

5-{3-[4-(1-Methyl-1H-imidazo[4,5-c]pyridin-4-yl)piperazin-1-yl]propyl}-1H-indole-3-carbonitrile oo)

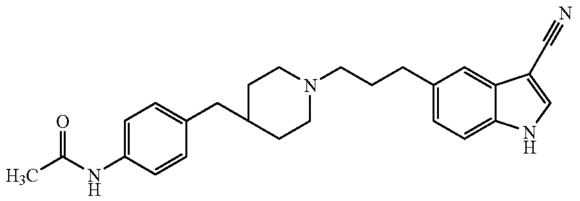

N-(4-{1-[3-(3-Cyano-1H-indol-5-yl)propyl]piperidin-4-ylmethyl}-phenyl)acetamide pp)

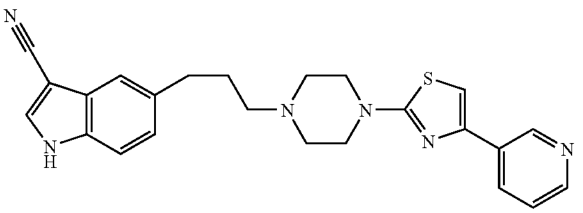

5-{3-[4-(4-Pyridin-3-ylthiazol-2-yl)piperazin-1-yl]propyl}-1H-indole-3-carbonitrile qq)

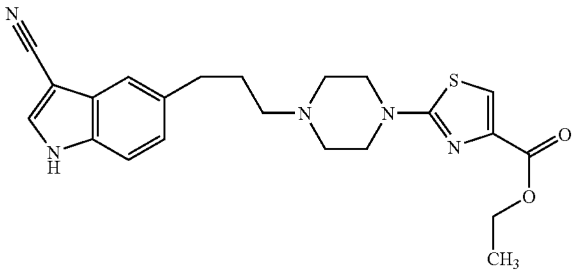

Ethyl 2-{4-[3-(3-cyano-1H-indol-5-yl)propyl]piperazin-1-yl}-thiazole-4-carboxylate rr)

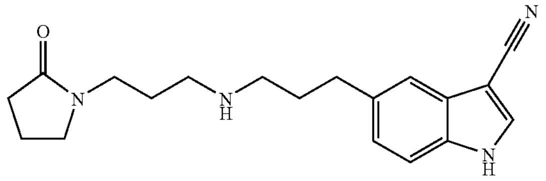

5-{3-[3-(2-Oxopyrrolidin-1-yl)propylamino]propyl}-1H-indole-3-carbonitrile ss)

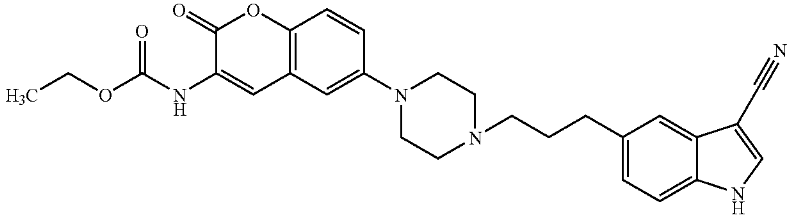

Ethyl(6-{4-[3-(3-Cyano-1H-indol-5-yl)propyl]piperazin-1-yl}-2-oxo-2H-chromen-3-yl)carbamate tt)

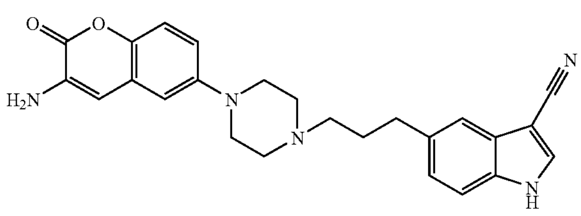

5-{3-[4-(3-Amino-2-oxo-2H-chromen-6-yl)piperazin-1-yl]propyl}-1H-indole-3-carbonitrile uu)

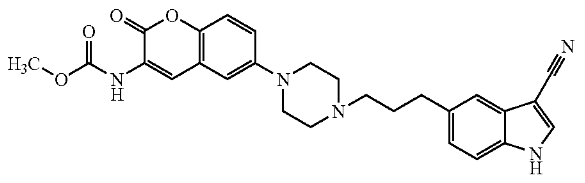

Methyl(6-{4-[3-(3-Cyano-1H-indol-5-yl)propyl]piperazin-1-yl}-2-oxo-2H-chromen-3-yl)carbamate vv)

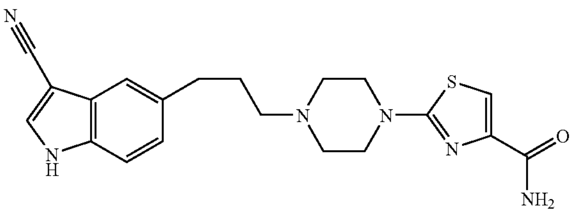

2-{4-[3-(3-Cyano-1H-indol-5-yl)propyl]piperazin-1-yl}-thiazole-4-carboxamide ww)

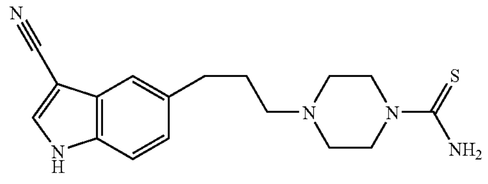

4-[3-(3-Cyano-1H-indol-5-yl)propyl]piperazin-1-thiocarboxamide and salts and solvates thereof, preferably physiologically tolerated salts and solvates thereof and in particular physiologically tolerated salts thereof.

Depending on the choice of the substituents and radicals described above, the compounds according to the invention can have one or more chiral centres, in particular one or more chiral carbon atoms. If a compound of defined composition according to the invention has one or more chiral centres, this compound of defined composition can exist in the form of various stereoisomers. The present invention relates to all possible such stereoisomers of compounds according to the invention, which can exist either as individual, stereochemically uniform compounds or as mixtures of two or more stereochemically uniform compounds. In the case of mixtures of two or more stereoisomers, the individual stereoisomers may be present in different or identical proportions. In mixtures of two stereoisomers which are present in identical proportions and represent optical antipodes, the term racemic mixtures is used. Racemic mixtures of compounds of the formula I are likewise a subject-matter of the present invention.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The starting materials, for example the compounds of the formula II and/or III, can, if desired, also be formed in situ by not isolating them from the reaction mixture, but instead immediately converting them further into the compound of the formula I.

The compound of the formula I can preferably be obtained by reacting compounds of the formula II with benzylpiperidine, phenoxypiperidine or derivatives thereof, in particular 4-(4-fluorobenzyl)piperidine, 4-(2,4-di-fluorobenzyl)piperidine or 4-(4-fluorophenoxy)piperidine.

The starting compounds of the formula II are generally novel. However, they can be prepared by methods known per se. The starting compounds of the formula III are either novel or known from the literature or commercially available. In any case, however, they can be prepared by methods known per se.

In the compounds of the formula II, $L^1$ is preferably Cl, Br, I, OH or a reactively modified OH group, in particular a reactively esterified OH group, such as an alkylsulfonyloxy group having 1-6 carbon atoms (preferably methylsulfonyloxy) or arylsulfonyloxy group having 6-10 carbon atoms (preferably phenyl- or p-tolylsulfonyloxy), or a diazonium group.

In the compounds of the formula III, $L^2$ is preferably H or a group which activates the amino function, for example a metal ion. Suitable metal ions are, in particular, alkali metal, alkaline earth metal or aluminium ions. Preferred metal ions are alkali metal ions, in particular Li, Na or K. In the case of polyvalent metal ions, a complex of metal ion and two or more compounds of the formula III often forms, where the complex generally comprises stoichiometrically as many compounds of the formula III as corresponds to the valency of the metal ion.

The reaction of the compounds of the formula II with compounds of the formula III is generally carried out in an inert solvent, preferably in the presence of an acid-binding agent. Suitable acid-binding agents are all bases which are usual in synthetic organic chemistry, both inorganic and organic bases, preferably organic bases. Examples of suitable organic bases are triethylamine, diisopropylamine (DIPEA), dimethylaniline, pyridine and quinoline. The addition of an inorganic base, such as, for example, an alkali or alkaline earth metal hydroxide, carbonate or bicarbonate, or another salt of a weak acid of the alkali or alkaline earth metals, preferably of potassium, sodium, calcium or caesium, may also be favourable.

The reaction time is, depending on the conditions used, between a few minutes and 14 days, and the reaction temperature is between about −30° and 180°, normally between −20° and 140°, preferably between −10° and 130° and in particular between about 0° and about 120°. In many cases, it is favourable to carry out the reaction of a starting compound of the formula II with a starting compound of the formula III at comparatively high temperatures, for example at a temperature in the range from 70° to 130°, preferably from 80° to 120° and in particular from 90° to 110°, for example at about 100°. In a reaction in this temperature range, it is in many cases favourable to use an organic base, such as triethylamine or diisopropylamine, or preferably an inorganic base, such as sodium hydroxide, sodium carbonate and in particular sodium hydrogencarbonate.

Suitable inert solvents are, for example, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, water, or mixtures of the said solvents.

The starting compounds of the formula II, in particular those in which X is $(CHR^7)_3$ and preferably a propylene radical, i.e. $CH_2CH_2CH_2$, can advantageously be prepared in a multistep synthesis sequence which starts from a compound of the formula VI

VI

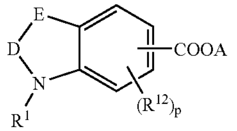

In a first step, the ester group COOA of the compound of the formula VI is reduced to a hydroxymethyl group $CH_2$—OH, for example using hydrides, preferably complex hydrides, such as lithium aluminium hydride. This gives a hydroxymethyl derivative of the formula VII

VII

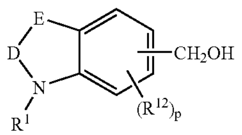

which can be converted in a second step using an oxidant, such as, for example, manganese dioxide ($MnO_2$), into an aldehyde derivative of the formula VIII

VIII

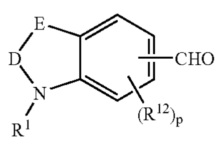

The aldehyde derivative of the formula VIII be condensed in a third reaction step with an acetic acid derivative $CH_3$—COOA, preferably ethyl acetate and in particular methyl acetate (aldol condensation). The condensation is preferably carried out under basic conditions, for example using alkoxides, such as sodium methoxide or sodium ethoxide, as base. This third step gives an acrylate derivative of the formula IX

IX

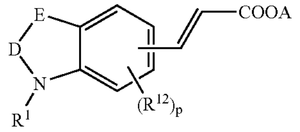

which can be hydrogenated in a fourth step to give a compound of the formula X

X

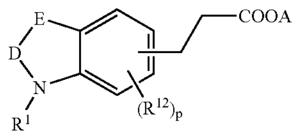

for example in a hydrogen atmosphere in the presence of a platinum metal catalyst, such as, for example, palladium/carbon. The compound of the formula X can subsequently be reduced in a fifth step to an alcohol derivative of the formula XI

XI

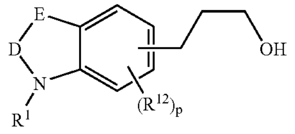

Suitable reducing agents for this step are, for example, metal or boron hydrides and in particular complex hydrides, such as lithium aluminium hydride, and so-called deactivated complex hydrides, such as $LiAl(OR)_xH_4$-X, in which X is 1, 2 or 3 and R are alkyl radicals having from 1 to of carbons. A deactivated complex hydride which is suitable for this reduction is commercially available under the name Vitride. The use of the so-called deactivated complex hydrides is particularly advantageous if it is desired to achieve selective reduction of the COOA group in the compound X to an alcohol group as in the formula XI in the presence of other groups which can be reduced by conventional hydrides, such as lithium aluminium hydride, such as, for example, nitrile groups. The compound XI is an example of a compound of the formula II in which X is $CH_2CH_2CH_2$ and $L^1$ is OH. A compound of the formula XI is preferably converted into a compound of the formula XII

XII

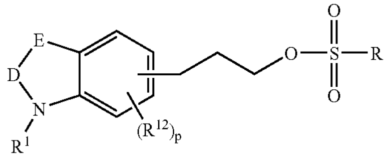

in which the OH group is reactively esterified, for example by reaction with alkyl- or arylsulfonyl chlorides, preferably in the presence of a base, such as, for example, alkylamines and in particular triethylamine or diisopropylamine. The compounds of the formula XI or preferably of the formula XII are subsequently reacted with a compound of the formula III in which $L^2$ is preferably H to give a compound of the formula I, preferably in the presence of a base, such as, for example, alkali metal hydroxides, alkali metal carbonates and in particular alkali metal hydrogencarbonates.

For the preparation of compounds of the formula I in which D-E is $R^2C{=}CR^4$ and $R^2$ and/or $R^4$ is CN, it is advantageous to start from compounds of the formula VI in which D-E is $R^2C{=}CR^4$ and $R^2$ and/or $R^4$ is H, and to convert these firstly, as described above, into compounds of the formulae VII, VII VIII and IX in which D-E is $R^2C{=}CR^4$ and $R^2$ and/or $R^4$ is H. The conversion of $R^2$ and/or $R^4$ from H into CN is then preferably carried out by firstly allowing dimethylformamide to react with phosphoryl chloride, adding a compound of the formula IX in which D-E is $R^2C{=}CR^4$ and $R^2$ and/or $R^4$ is H and in particular a compound of the formula IXa in which D-E is $R^2C{=}CR^4$ and $R^2$ and $R^4$ is H, allowing the reaction mixture to react, preferably at a temperature between 50 and 150° C. and in particular from 80 to 130° C., preferably for a time in the range from ten minutes to two hours and in particular from 30 to 90 minutes. The reaction mixture is subsequently reacted with hydroxylammonium chloride (=hydroxylamine hydrochloride). The reaction with hydroxylammonium chloride is preferably carried out in a temperature range as described above and for a period of from 2 to 60 minutes and in particular from 5 to 30 minutes. For work-up, the reaction mixture is preferably hydrolysed, and the compound of the formula IX in which D-E is $R^2C{=}CR^4$ and $R^2$ and/or $R^4$ is CN, or, if a compound of the formula IXa has been employed, the compound of the formula IXb in which D-E is $R^2C{=}CR^4$ and $R^2$ is H and $R^4$ is CN is isolated by conventional methods which are familiar to the person skilled in the art.

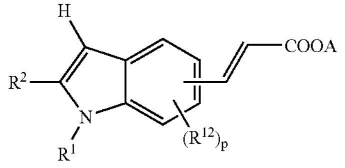

IXa (compound IX where
D - E = $R^2C = CR^4$; $R^4$ = H)

1. DMF/$POCl_3$
2. $NH_2OH$ x HCl

Δ

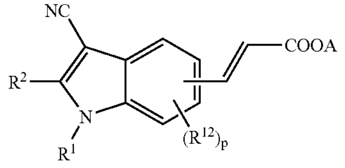

IXb (compound IX where
D - E = $R^2C = CR^4$; $R^4$ = CN)

The above process is particularly suitable for the conversion of compounds of the formula IX in which D-E is $R^2C{=}CR^4$ and $R^2$ and $R^4$ is H into compounds of the formula IX in which D-E is $R^2C{=}CR^4$, $R^2$ is H and $R^4$ is CN.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

The compounds according to the invention can be used as therapeutic agents, diagnostic agents and/or cosmetics or together with one or more active ingredients other than the compounds according to the invention and/or adjuvants in therapeutic agents, diagnostic agents and/or cosmetics. The compounds according to the invention are usually employed in the form of pharmaceutical, diagnostic and/or cosmetic formulations. Formulations of this type and processes for the preparation thereof are known to the person skilled in the art.

Examples of formulations of this type are suspensions, emulsions, solutions, liposomes, salts, pastes, biodegradable polymers, nanoparticles, tablets, coated tablets, sugar-coated tablets, film-coated tablets, capsules, pills, granules, powders, aerosols, drops or sprays comprising at least one compound according to the invention.

The compounds according to the invention or formulations which comprise at least one compound according to the invention can be administered to humans or animals, for example locally or systemically and in particular orally, intravenously, intraperitoneally, subcutaneously, transdermally, nasally, buccally and/or iontophoretically.

The invention furthermore relates to the use of the compounds of the formula I and/or physiologically acceptable salts thereof for the preparation of pharmaceutical preparations, in particular by non-chemical methods. They can be converted here into a suitable dosage form together with at least one solid, liquid and/or semi-liquid excipient or adjuvant and, if desired, in combination with one or more further active ingredients.

The invention furthermore relates to pharmaceutical preparations comprising an effective amount of at least one of the compounds of the formula I and/or one of its physiologically acceptable salts thereof.

These preparations can be used as medicaments in human or veterinary medicine. Suitable excipients are organic or inorganic substances which are suitable for enteral (for example oral), parenteral or topical administration or administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, sugar-coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, to prepare injection preparations. The preparations indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically tolerated solvents may be present, for example ethanol. Inhalation solutions can be administered with the aid of conventional inhalers.

The present invention therefore relates to a process for the preparation of pharmaceutical compositions which is characterised in that a compound of the formula I according to claim 1 and/or one of its physiologically acceptable salts and/or solvates is converted into a suitable dosage form together with at least one solid, liquid or semi-liquid excipient or adjuvant.

The compounds of the formula I and/or physiologically acceptable salts thereof can be used as excitatory amino acid antagonists for combating diseases, in particular for combating neurodegenerative diseases, including cerebrovascular diseases, epilepsy, schizophrenia, Alzheimer's disease, Parkinson's disease, Huntington's disease, cerebral ischaemia, infarction or psychoses.

The present invention therefore relates to the use of compounds of the formula I according to claim 1 and/or physiologically acceptable salts or solvates thereof for the preparation of a medicament for the prophylaxis and/or treatment of schizophrenia, depression, dementia, Parkinson's disease, Alzheimer's disease, Lewy bodies dementia, Huntington's disease, Tourette's syndrome, anxiety, learning and memory impairment, neurodegenerative diseases and other cognitive impairments, as well as nicotine dependence and pain.

In general, the compounds according to the invention can be administered analogously to other known compounds having a similar action profile, such as, for example, ifenprodil, preferably in doses between about 0.05 and 500 mg, in particular between 0.5 and 100 mg, per dosage unit. The daily dose is preferably between about 0.01 and 2 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Parenteral administration is preferred. Oral administration is particularly preferred.

The compounds according to the invention exhibit an advantageous action profile while being comparatively easy to prepare. Thus, in receptor binding tests, compounds according to the invention exhibit an affinity to the ifenprodil binding site of the NMDA receptor, even in nanomolar concentrations. In addition, the compounds according to the invention, as polyamine antagonists which preferentially bind selectively to the NR2B receptor of the NMDA subreceptor class, are preferably distinguished by no or and only very slight elongation of the QT segment in the electrocardiogram.

The compounds of the formula I and pharmaceutically usable prodrugs, derivatives, solvates, stereoisomers and salts thereof are particularly preferably suitable for the treatment of diseases of the central nervous system, such as states of tension, depression, anxiety states, schizophrenia, gastrointestinal tract disorders, nausea, tardive dyskinesia, Parkinson's disease and/or psychoses and of side effects in the treatment of hypertonia (for example using $\alpha$-methyldopa). The compounds can furthermore advantageously be used in endocrinology and gynaecology, for example for the therapy of acromegaly, hypogonadism, secondary amenorrhoea, premenstrual syndrome, undesired puerperal lactation, furthermore for the prophylaxis and therapy of cerebral disorders (for example migraine), in particular in geriatrics, in a similar way to certain ergot alkaloids.

The compounds according to the invention can also very particularly preferably be employed as therapeutic agents for combating the consequences of cerebral infarction (apoplexia cerebri), such as strokes and cerebral ischaemia, and for the treatment of brain and spinal cord trauma.

The compounds according to the invention are particularly suitable as medicament active ingredients for anxiolytics, antidepressants, anti-psychotics, neuroleptics, antihypertonics and/or for positively influencing obsessive-compulsive disorder (OCD), sleeping disorders, tardive dyskinesia, learning disorders, age-related memory disorders, eating disorders, such as bulimia, and/or sexual dysfunctions.

For the above-mentioned indications/areas of application, preferably for the indications/areas of application mentioned in the two preceding paragraphs, the substances according to the invention are generally administered analogously to known commercially available preparations (for example citalopram and fluoxetine), preferably in doses of between about 0.2 and 500 mg, in particular between 0.2 and 50 mg, per dosage unit. The daily dose is preferably between about 0.001 and 10 mg/kg of body weight. The low doses are between about 0.2 and 500 mg, in particular between 0.2 and 50 mg, per dosage unit. The low doses (from about 0.2 to 1 mg per dosage unit; from about 0.001 to 0.005 mg/kg of body weight) are particularly suitable for use as migraine agents; for the other indications, doses of between 10 and 50 mg per dosage unit are preferred. However, the specific dose for each particular patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred for the above-mentioned indications.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, if necessary the organic phase is dried, for example over sodium sulfate, the organic phase is evaporated, and the residue obtained is purified by chromatography, for example on silica gel, and/or by crystallisation.

EXAMPLE 1

Preparation of 4-{3-[4-(fluorobenzyl)piperidin-1-yl]propyl}-1H-indole-3-carbonitrile (=EMD 432517)

1.1. Step a: Preparation of 4-hydroxymethylindole (2)

A solution of 25 g of methyl 4-indolecarboxylate (1) in 200 ml of tetrahydrofuran is added to a suspension of $LiAlH_4$ in 100 ml of tetrahydrofuran under a protective-gas atmosphere ($N_2$) at such a rate that the temperature of the reaction mixture does not exceed 40° C. When the addition is complete, the reaction mixture is stirred at room temperature (25° C.) for approximately two further hours until the methyl 4-indolecarboxylate has reacted completely. The reaction mixture is subsequently hydrolysed by addition of ice-water (about 100 ml), and the hydrolysate is filtered through a bed of kieselguhr. After the tetrahydrofuran has been removed by distillation, the aqueous phase obtained is extracted with ethyl acetate. The organic phase obtained is dried over magnesium sulfate and evaporated, giving 16.0 g (76% of theory) of a pale-beige crystalline residue of 4-hydroxymethylindole (2).

1.2. Step b: preparation of 4-formylindole (3)

Manganese dioxide ($MnO_2$) is added slowly with stirring to a solution of 74 g of 4-hydroxymethylindole (2) in 3 litres of dichloromethane, and the mixture is subsequently stirred at room temperature for 72 hours. The reaction mixture is subsequently filtered through kieselguhr, and the filtrate is evaporated. The crystalline residue obtained is stirred with cyclohexane and filtered under reduced pressure. Drying gives 63 g (86% of theory) of crystalline 4-formylindole (3).

1.3. Step c: Preparation of methyl 3-(1H-indol-4-yl)acrylate (4)

48 g of sodium methoxide are added to 300 ml of tetrahydrofuran with stirring at 5° C. under a protective gas ($N_2$), the suspension is cooled to 0° C., 70 ml of methyl acetate are added dropwise at from 0 to 3° C., and the mixture is stirred at this temperature for a further 45 minutes. A solution of 43 g of 4-formylindole (3) in 300 ml of tetrahydrofuran is subsequently added with stirring, during which the temperature does not exceed 3° C. The mixture is subsequently stirred at room temperature for a further two hours. For work-up, the reaction mixture is evaporated, and the residue is dissolved in methyl acetate and extracted with water. The organic phase obtained is dried, the solvent is removed under reduced pressure, and the residue is purified by chromatography on silica gel, giving 35 g (59% of theory) of a pale-beige crystalline residue of methyl 3-(1H-indol-4-yl)acrylate (4).

1.4. Step d: Preparation of Indolecarbonitrile 5

Phosphoryl chloride is added dropwise with cooling in an ice bath to 100 ml of dimethylformamide at such a rate that the temperature of the mixture is from about 20 to 30° C. A solution of 25 g of 3-(1H-indol-4-yl)acrylic acid in 100 ml of dimethylformamide is subsequently added dropwise at room temperature, during which the temperature rises to 60° C. The mixture is subsequently stirred at 125° C. for one hour. A warm solution of 17.2 g of hydroxylammonium chloride in 100 ml of dimethylformamide is then added, and the mixture is stirred at 120° C. for a further 15 minutes. The reaction mixture is cooled to room temperature and added dropwise with stirring to ice-water, whereupon beige crystals precipitate. The mixture is stirred for a further two hours and filtered, and the crystalline residue is dried overnight at 120° C. under reduced pressure, giving 23.5 g (84% of theory) of a pale-beige crystalline residue of indolecarbonitrile 5.

1.5. Step e: Preparation of Compound 6

5 g of indolecarbonitrile 5 are dissolved in methanol under a protective-gas atmosphere ($N_2$), palladium on active carbon (Pd/C) is added, and the mixture is hydrogenated at room temperature under atmospheric pressure with hydrogen until the reaction is complete. For work-up, the reaction mixture is filtered, and the filtrate is freed from solvent under reduced pressure. The residue is taken up in methyl acetate and extracted with water. The organic phase is separated off, dried and evaporated. The residue is purified by chromatography on silica gel using ethyl acetate as eluent, giving 4.2 g (84% of theory) of a beige crystalline residue of compound 6.

1.6. Step f: Preparation of Compound 7

18.2 g of compound 6 are dissolved in 1000 ml of tetrahydrofuran under a protective-gas atmosphere, and the solution is cooled to 0° C. A solution of 60 ml of Vitride in 60 ml of toluene is subsequently added dropwise at such a rate that the temperature remains in the range from 2 to 8° C., and the mixture is stirred at 5° C. for a further three hours. During the addition of the Vitride, a precipitate may form, which, however, generally re-dissolves on subsequent stirring. Excess Vitride is hydrolysed by addition of 250 ml of water, during which a precipitate may form. A further 200 ml of water and 300 ml of ethyl acetate are added, and the mixture is left to stand overnight. The reaction mixture is subsequently filtered through kieselguhr, the residue is discarded, and the filtrate phases are separated. The organic phase is freed from solvent under reduced pressure and purified by chromatography on silica gel using ethyl acetate as eluent, giving 13.5 g (84% of theory) of a beige crystalline residue of compound 7.

1.7. Step g: Preparation of Compound 8

A solution of 6 g of compound 7 in 80 ml of dichloromethane and 80 ml of tetrahydrofuran is cooled to 2° C. 2.3 ml of methanesulfonyl chloride are added, the mixture is stirred briefly, and 5.3 ml of triethylamine are subsequently added at from 2 to 5° C. The mixture is subsequently stirred at 2° C. for a further 2 hours. The reaction mixture is then poured into ice-water, the aqueous phase is extracted, and the combined organic phases are freed from solvent under reduced pressure, giving 7.6 g (91% of theory) of a brown crystalline residue of compound 8.

1.8. Step h: Preparation of Compound 10

0.40 gram of 4-(4-fluorobenzyl)piperidine (9) and 0.42 gram of sodium hydrogencarbonate are added to a suspension of 0.50 gram of compound 8 in 10 ml of acetonitrile with stirring, and the mixture is stirred at 100° C. for 24 hours. The reaction mixture is subsequently cooled to room temperature, and the solvent is removed under reduced pressure. The residue obtained is purified by chromatography on silica gel and dissolved in acetone, and ethereal hydrochloric acid is added. The crystalline precipitate which forms is separated off by filtration and dried, giving 230 mg (35% of theory) of compound 10 (4-{3-[4-(4-fluorobenzyl)-1-pipendyl]propyl}-1H-indole-3-carbonitrile as the hydrochloride.

The following formula scheme relates to the preparation of 4-{3-[4-(4-fluorobenzyl)-1-piperidyl]propyl}-1H-indole-3-carbonitrile in accordance with Example 1. The lower-case letters a to h on the reaction arrows correspond to reaction steps a to h described above.

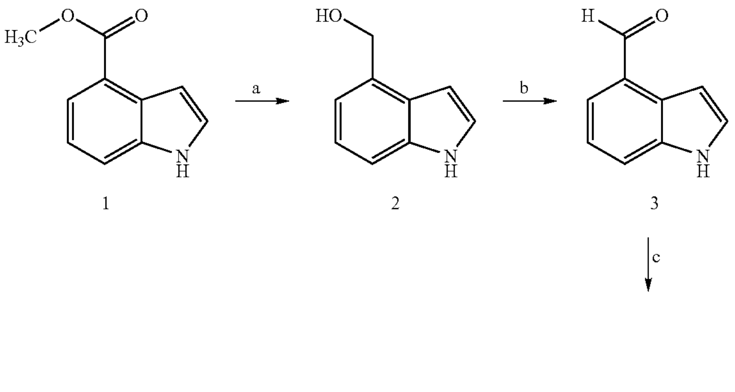

1 2 3

-continued
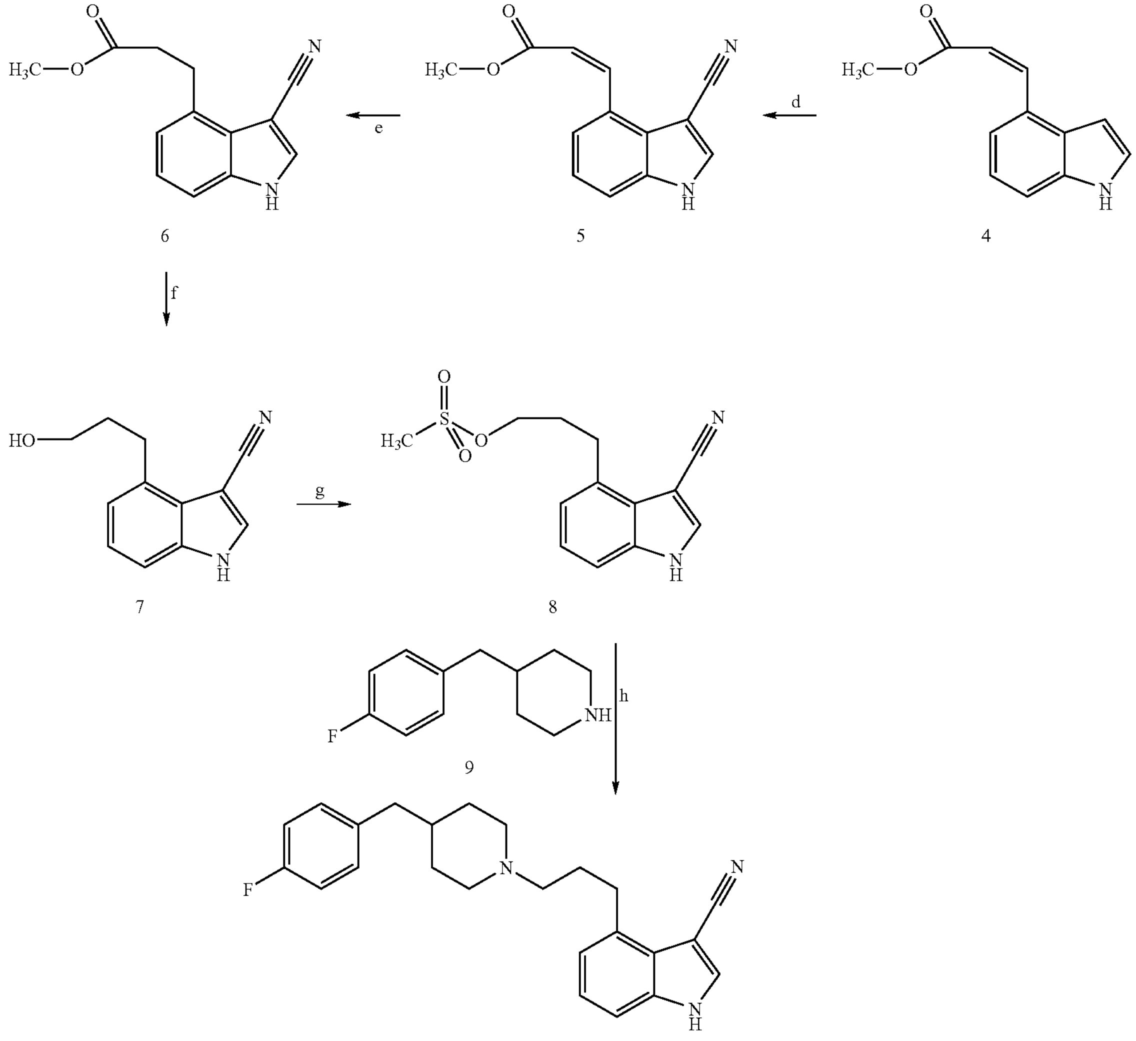
4 5 6 7 8 9 10
EXAMPLE 2
Process steps a' to g': preparation of compound 18 Compound 18 was obtained analogously to the reaction sequence carried out in Example 1 in reaction steps a to g in accordance with the following formula scheme in reaction steps a' to h'.
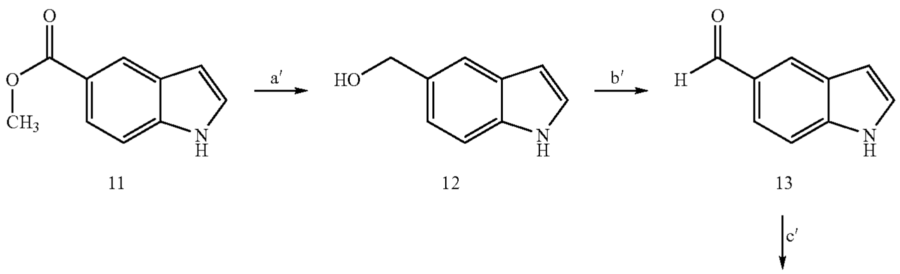
11 12 13

-continued

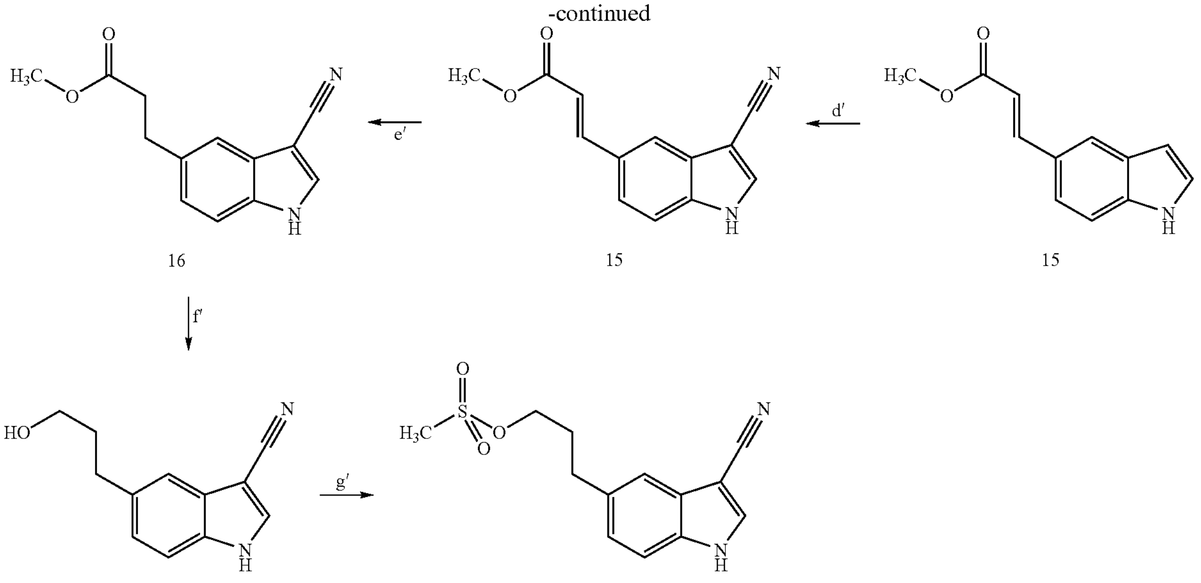

16 15 15

17 18

5-{4-[3-(3-Cyano-1H-indol-5-yl)propyl]piperazin-1-yl}benzofuran-2-carboxamide 20 can be obtained analogously to process step h of Example 1 in accordance with the following conditions by reaction of compound 18 with compound 19:

Step h': Preparation of Compound 20

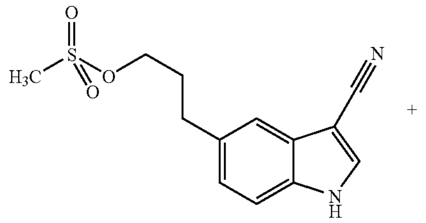

18

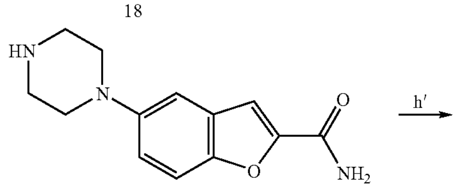

19

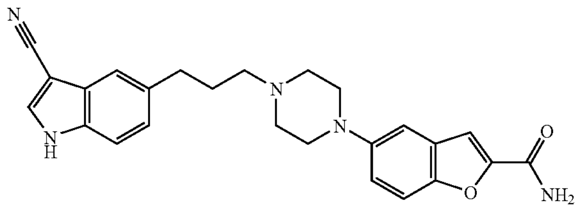

20

0.90 g of 5-piperazin-1-ylbenzofuran-2-carboxamide (19) and 1.4 g of ethyldiisopropylamine (DIPEA) are added with stirring to a suspension of 1.00 gram of compound 18 in 30 ml of acetonitrile, and the mixture is refluxed for 18 hours. The reaction mixture is subsequently cooled to room temperature, methanol (20 ml) is added, and the mixture is refluxed for a further three hours. The solvent is subsequently removed under reduced pressure, and the residue is purified by chromatography on silica gel. The residue obtained is dissolved in acetone, and ethereal hydrochloric acid is added. The crystalline precipitate which forms is separated off by filtration and dried, giving 0.4 g (22% of theory) of the compound 5-{4-[3-(3-cyano-1H-indol-5-yl)propyl]piperazin-1-yl}benzofuran-2-carboxamide 20 as the hydrochloride.

EXAMPLE 3

The following compounds can be obtained analogously to the process described in Example 1 or Example 2:

5-{3-[4-(4-Cyanophenyl)piperazin-1-yl]propyl}-1H-indole-3-carbonitrile (21);

5-{4-[3-(3-Cyano-1H-indol-6-yl)propyl]piperazin-1-yl}benzofuran-2-carboxamide (22);

5-{3-[4-(2-Oxo-2H-chromen-6-yl)piperazin-1-yl]propyl}-1H-indole-3-carbonitrile (23);

5-{4-[3-(3-Cyano-1H-indol-4-yl)propyl]piperazin-1-yl}benzofuran-2-carboxamide (24);

5-{3-[4-(1H-indol-4-yl)piperazin-1-yl]propyl}-1-methanesulfonyl-1H-indole-3-carbonitrile (25);

5-[3-(4-Oxo-1-phenyl-1,3,8-triazaspiro[4.5]dec-8-yl)propyl]-1H-indole-3-carbonitrile (26);

5-[3-(4-Benzo[1,2,5]thiadiazol-4-ylpiperazin-1-yl)propyl]-1H-indole-3-carbonitrile (27);

3-{1-[3-(3-Cyano-1H-indol-5-yl)propyl]piperidin-4-yl}-1H-indole-5-carboxamide (8);

5-[3-(4-Quinolin-8-ylpiperazin-1-yl)propyl]-1H-indole-3-carbonitrile (29);

5-{3-[4-(2,3-Dihydrobenzo[1,4]dioxin-5-yl)piperazin-1-yl]propyl}-1H-indole-3-carbonitrile (30);

1-Methanesulfonyl-5-[3-(4-oxo-1-phenyl-1,3,8-triazaspiro[4.5]dec-8-yl)propyl]-1H-indole-3-carbonitrile (31);

5-{3-[4-(1H-indol-4-yl)piperazin-1-yl]propyl}-1H-indole-3-carbonitrile (32);

5-{3-[4-(1H-indol-3-yl)piperidin-1-yl]propyl}-1H-indole-3-carbonitrile (33);

5-{3-[4-(5-Fluoro-1H-indol-3-yl)piperidin-1-yl]propyl}-1H-indole-3-carbonitrile (34);

3-{1-[3-(3-Cyano-1H-indol-5-yl)propyl]piperidin-4-yl}-1H-indole-5-carbonitrile (35);

5-{3-[4-(6-Fluoro-1H-indol-3-yl)piperidin-1-yl]propyl}-1H-indole-3-carbonitrile (36);

5-{3-[4-(4-Fluoro-1H-indol-3-yl)piperidin-1-yl]propyl)}-1H-indole-3-carbonitrile (7);

5-[3-(4-Benzo[d]isothiazol-3-ylpiperazin-1-yl)propyl]-1H-indole-3-carbonitrile (38);

4-{3-[3-(3-Cyano-1H-indol-6-yl)propyl]piperidin-4-yloxy}-benzamide (39);

6-{3-[4-(2-Cyano-3-methoxyphenyl)piperazin-1-yl]propyl}-1H-indole-3-carbonitrile (40);

6-{3-[4-(4-Cyano-3-methoxyphenyl)piperazin-1-yl]propyl}-1H-indole-3-carbonitrile (41);

6-{3-[4-(4-Cyano-2-methoxyphenyl)piperazin-1-yl]propyl}-1H-indole-3-carbonitrile (42);

4-[3-(4-Pyrazol-1-ylmethyl-1-piperidyl)propyl]-1H-indole-3-carbonitrile (43);

6-{3-[4-(4-Fluorobenzyl)-1-piperidyl]propyl}-1H-indole-3-carbonitrile (44);

6-{3-[4-(2,4-Difluorobenzyl)-1-piperidyl]propyl}-1H-indole-3-carbonitrile (45);

6-{3-[4-(4-Fluorophenoxy)-1-piperidyl]propyl}-1H-indole-3-carbonitrile (46);

4-{3-[4-(2,4-Difluorobenzyl)-1-piperidyl]propyl}-1H-indole-3-carbonitrile (47);

4-{3-[4-(4-Fluorophenoxy)-1-piperidyl]propyl}-1H-indole-3-carbonitrile (48);

5-{3-[4-(4-Fluorophenoxy)-1-piperidyl]propyl}-1H-indole-3-carbonitrile (49);

5-{3-[4-(4-Fluorobenzyl)-1-piperidyl]propyl}-1H-indole-3-carbonitrile (50);

5-{3-[4-(2,4-Difluorobenzyl)-1-piperidyl]propyl}-1H-indole-3-carbonitrile (51).

The compounds can be purified and/or characterised by HPLC chromatography. The characterisation of the compounds via the retention time ($R_t$) can be carried out on a 3μ Silica-Rod column with a 210 second gradient from 20 to 100% water/acetonitrile/0.01% trifluoroacetic acid at a flow rate of 2.2 ml/minute and detection at a wavelength of 220 nanometres. Physical constants and analytical data (mass spectrometric data (HPLC-MS)) of compounds 20-43 synthesised as above are shown in Table I.

TABLE I

| Compound | Structure | MW g/mol | [M + H] HPLC-MS | $R_t$(HPLC)/ min |
|---|---|---|---|---|
| 20 | 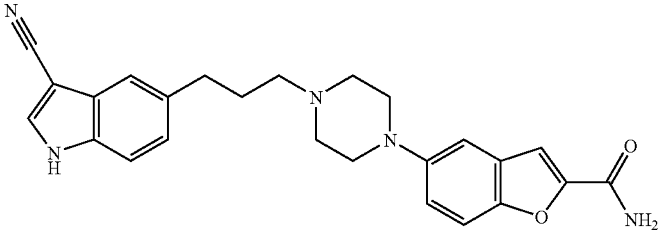 | | 429 | |
| 21 | 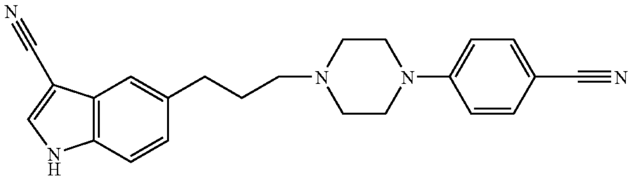 | | 370 | |
| 22 | 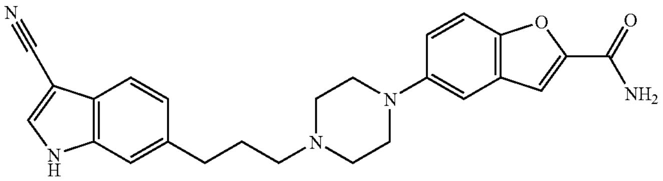 | | 429 | |
| 23 | 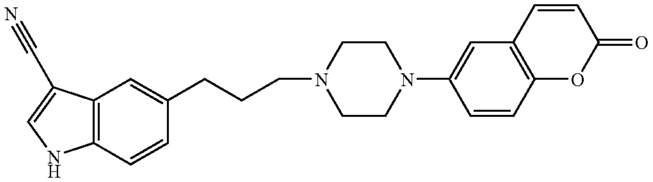 | | 413 | |

TABLE I-continued
| Compound | Structure | MW g/mol | [M + H] HPLC-MS | $R_t$(HPLC)/ min |
|---|---|---|---|---|
| 24 | 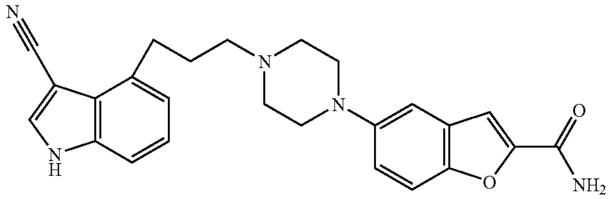 | | 429 | |
| 25 | 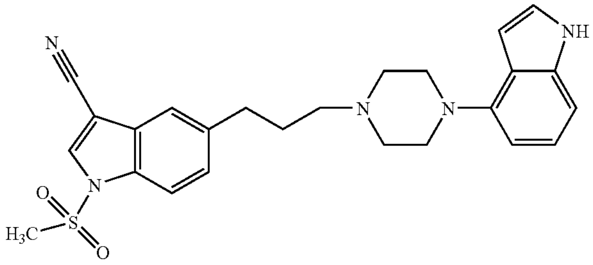 | | 463 | |
| 26 | 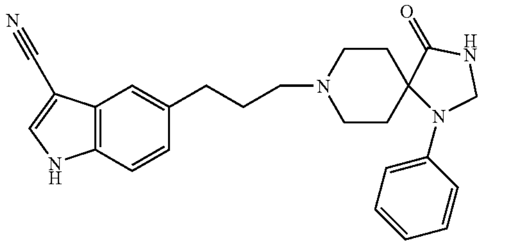 | | 415 | |
| 27 | 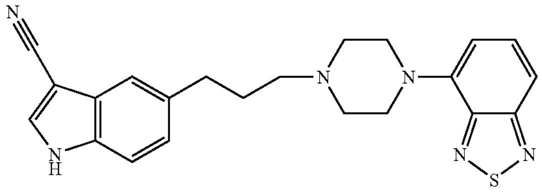 | | 404 | |
| 28 | 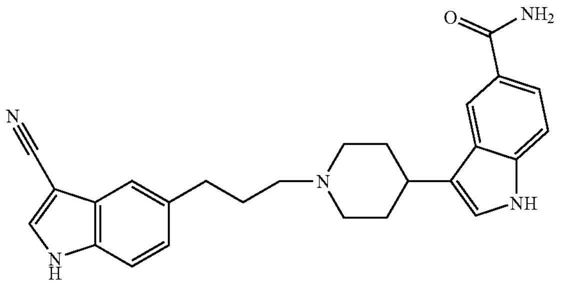 | | 426 | |
| 29 | 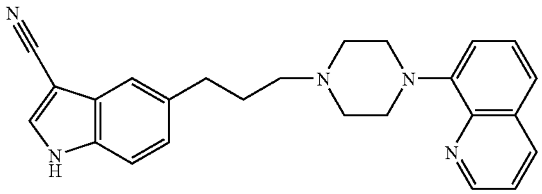 | | 397 | |

TABLE I-continued
| Compound | Structure | MW g/mol | [M + H] HPLC-MS | $R_t$(HPLC)/min |
|---|---|---|---|---|
| 30 | 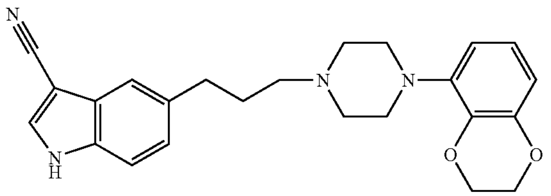 | | 403 | |
| 31 | 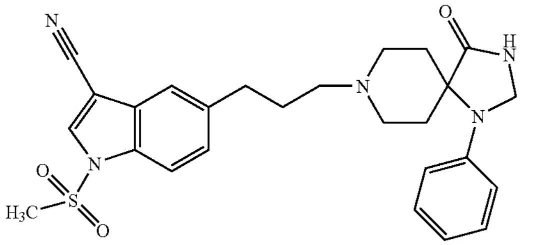 | | 493 | |
| 32 | 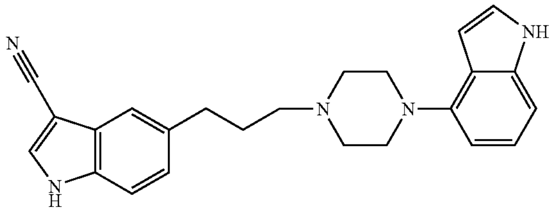 | | 384 | |
| 33 | 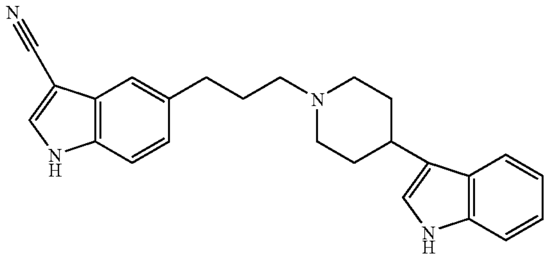 | | 384 | |
| 34 | 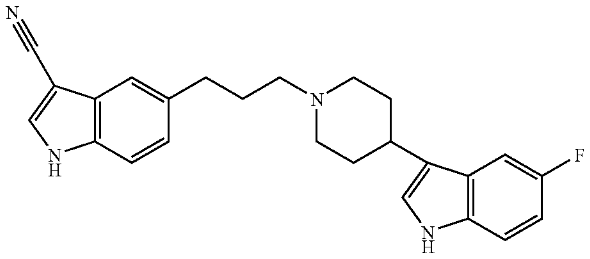 | | 401 | |
| 35 | 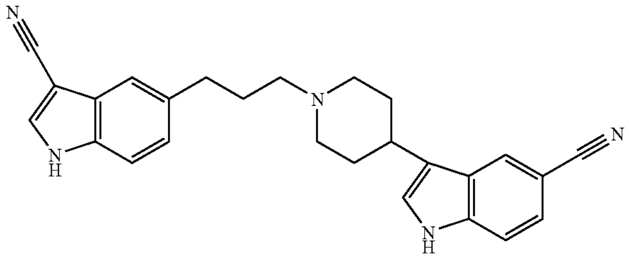 | | 409 | |

TABLE I-continued
| Compound | Structure | MW g/mol | [M + H] HPLC-MS | $R_t$(HPLC)/min |
|---|---|---|---|---|
| 36 | 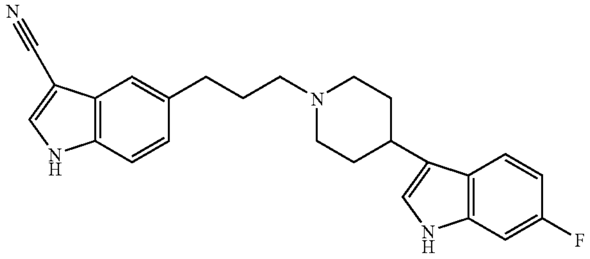 | | 401 | |
| 37 | 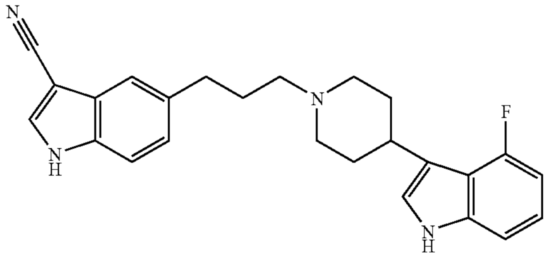 | | 401 | |
| 38 | 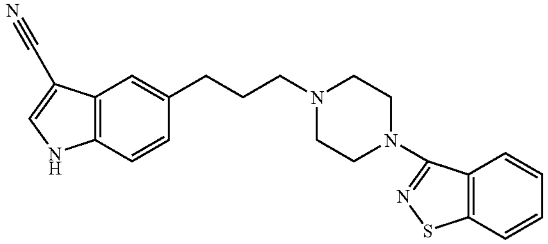 | | 403 | |
| 39 | 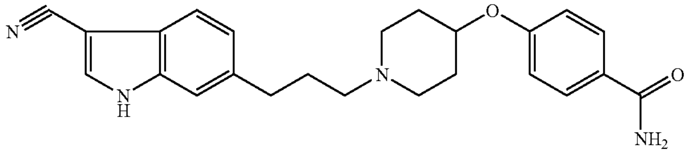 | | 403 | |
| 40 | 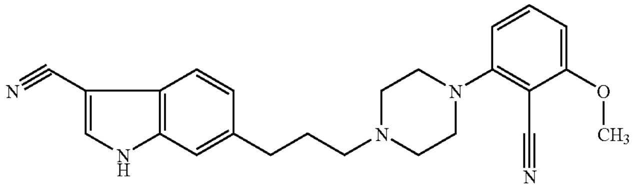 | | 400 | |
| 41 | 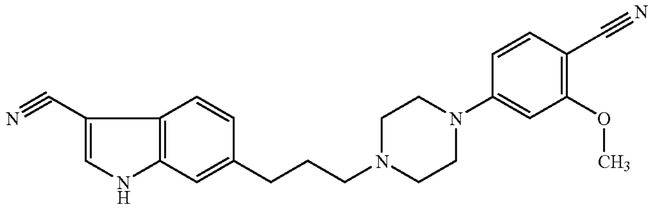 | | 400 | |

TABLE I-continued
| Compound | Structure | MW g/mol | [M + H] HPLC-MS | $R_t$(HPLC)/ min |
|---|---|---|---|---|
| 42 | 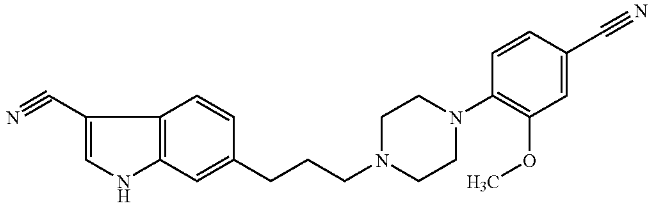 | | 400 | |
| 43 | 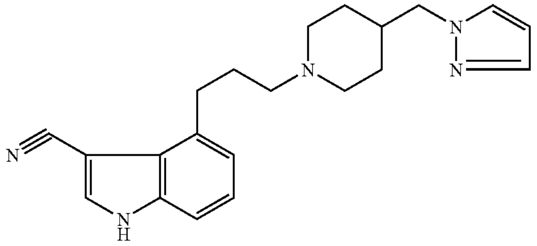 | | 348 | |
Physical constants and analytical data (mass spectrometric data (FAB-MS) and retention times (HPLC)) of compounds 10 and 44-51 synthesised as above are shown in Table II.
TABLE II
| Compound | Structure | MW g/mol | [M + H] HPLC-MS | $R_t$(HPLC)/ min |
|---|---|---|---|---|
| 10 | 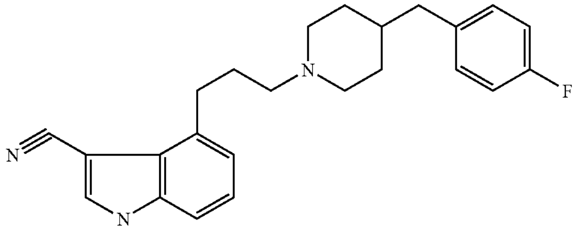 | 375.49 | 376.20 | 1.428 |
| 44 | 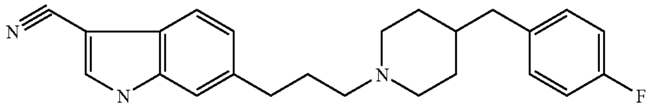 | 375.49 | 376 | 1.203 |
| 45 | 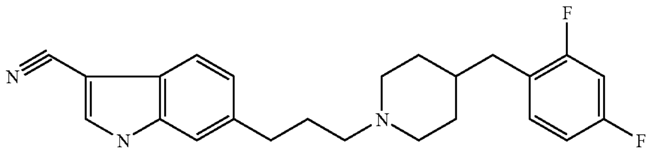 | 393.48 | 394 | 1.236 |
| 46 | 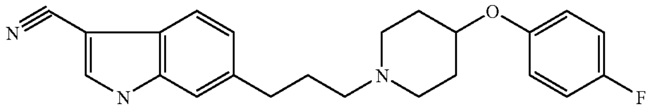 | 377.47 | 378 | 1.172 |

TABLE II-continued

| Compound | Structure | MW g/mol | [M + H] HPLC-MS | $R_t$(HPLC)/ min |
|---|---|---|---|---|
| 47 | 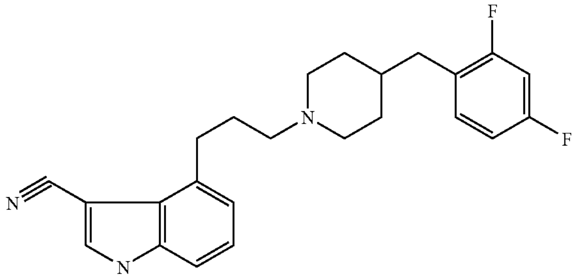 | 393.48 | 394 | 1.443 |
| 48 | 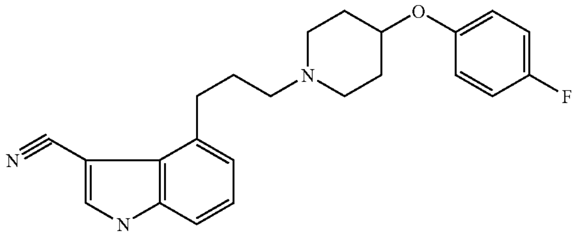 | 377.47 | 378 | 1.347 |
| 49 | 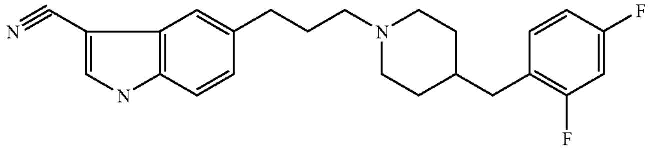 | | 394 | |
| 50 | 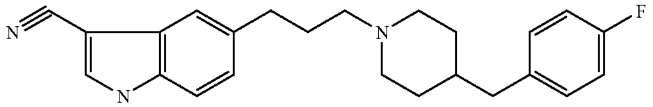 | | 376 | |
| 51 | 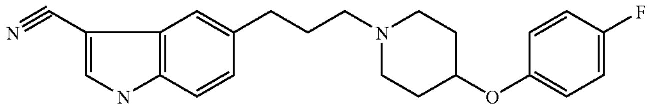 | | 378 | |

The examples below relate to pharmaceutical compositions:

EXAMPLE A

Injection Vials

A solution of 100 g of the active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of the active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of the active ingredient of the formula I, 9.38 g of $NaH_2PO_4$ $2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of the active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

We claim:

1. A compound which is a) 6-{3-[4-(4-fluorobenzyl)-1-piperidyl]propyl}-1H-indole-3-carbonitrile;

b) 6-{3-[4-(2,4-difluorobenzyl)-1-piperidyl]propyl}-1H-indole-3-carbonitrile;

c) 6-{3-[4-(4-fluorophenoxy)-1-piperidyl]propyl}-1H-indole-3-carbonitrile;

d) 4-{3-[4-(4-fluorobenzyl)-1-piperidyl]propyl}-1H-indole-3-carbonitrile;

e) 4-{3-[4-(2,4-difluorobenzyl)-1-piperidyl]propyl}-1H-indole-3-carbonitrile;

f) 4-{3-[4-(4-fluorophenoxy)-1-piperidyl]propyl}-1H-indole-3-carbonitrile;

g) 5-{3-[4-(4-fluorophenoxy)-1-piperidyl]propyl}-1H-indole-3-carbonitrile;

h) 5-{3-[4-(4-fluorobenzyl)-1-piperidyl]propyl}-1H-indole-3-carbonitrile;

i) 5-{3-[4-(2,4-difluorobenzyl)-1-piperidyl]propyl}-1H-indole-3-carbonitrile;

j) 5-{3-[4-(4-cyanophenyl)piperazin-1-yl]propyl}-1H-indole-3-carbonitrile;

k) 5-{4-[3-(3-cyano-1H-indol-6-yl)propyl]piperazin-1-yl}benzofuran-2-carboxamide;

l) 5-{3-[4-(2-oxo-2H-chromen-6-yl)piperazin-1-yl]propyl}-1H-indole-3-carbonitrile;

m) 5-{4-[3-(3-cyano-1H-indol-4-yl)propyl]piperazin-1-yl}-benzofuran-2-carboxamide;

n) 5-{4-[3-(3-cyano-1H-indol-5-yl)propyl]piperazin-1-yl}-benzofuran-2-carboxamide;

o) 5-{3-[4-(1H-indol-4-yl)-piperazin-1-yl]propyl}-1-methanesulfonyl-1H-indole-3-carbonitrile;

p) 5-[3-(4-oxo-1-phenyl-1,3,8-triazaspiro[4.5]dec-8-yl)propyl]-1H-indole-3-carbonitrile;

q) 5-[3-(4-benzo[1,2,5]thiadiazol-4-ylpiperazin-1-yl)propyl]-1H-indole-3-carbonitrile;

r) 3-{1-[3-(3-cyano-1H-indol-5-yl)propyl]piperidin-4-yl}-1H-indole-5-carboxamide;

s) 5-[3-(4-quinolin-8-ylpiperazin-1-yl)propyl]-1H-indole-3-carbonitrile;

t) 5-{3-[4-(2,3-dihydrobenzo[1,4]dioxin-5-yl)piperazin-1-yl]propyl}-1H-indole-3-carbonitrile;

u) 1-methanesulfonyl-5-[3-(4-oxo-1-phenyl-1,3,8-triazaspiro[4.5]dec-8-yl)propyl]-1H-indole-3-carbonitrile;

v) 5-{3-[4-(1H-indol-4-yl)piperazin-1-yl]propyl}-1H-indole-3-carbonitrile;

w) 5-{3-[4-(1H-indol-3-yl)piperidin-1-yl]propyl}-1H-indole-3-carbonitrile;

x) 5-{3-[4-(5-fluoro-1H-indol-3-yl)piperidin-1-yl]propyl}-1H-indole-3-carbonitrile;

y) 3-{1-[3-(3-cyano-1H-indol-5-yl)propyl]piperidin-4-yl}-1H-indole-5-carbonitrile;

z) 5-{3-[4-(6-fluoro-1H-indol-3-yl)piperidin-1-yl]propyl}-1H-indole-3-carbonitrile;

aa) 5-{3-[4-(4-fluoro-1H-indol-3-yl)piperidin-1-yl]propyl}-1H-indole-3-carbonitrile;

bb) 5-[3-(4-benzo[d]isothiazol-3-ylpiperazin-1-yl)propyl]-1H-indole-3-carbonitrile;

cc) 4-{1-[3-(3-cyano-1H-indol-6-yl)propyl]piperidin-4-yloxy}benzamide;

dd) 6-{3-[4-(2-cyano-3-methoxyphenyl)piperazin-1-yl]propyl}-1H-indole-3-carbonitrile;

ee) 6-{3-[4-(4-cyano-3-methoxyphenyl)piperazin-1-yl]propyl}-1H-indole-3-carbonitrile;

ff) 6-{3-[4-(4-cyano-2-methoxyphenyl)piperazin-1-yl]propyl}-1H-indole-3-carbonitrile;

gg) 4-[3-(4-pyrazol-1-ylmethy-1-piperidyl)propyl]-1H-indole-3-carbonitrile;

hh) N-(6-{4-[3-(3-cyano-1H-indol-5-yl)propyl]piperazin-1-yl}-2-oxo-2H-chromen-3-yl)acetamide;

ii) 5-{3-[(pyridin-3-ylmethyl)amino]propyl}-1H-indole-3-carbonitrile;

jj) 5-{3-[4-(2,3-dihydrobenzo[1,4]dioxin-6-yl)piperazin-1-yl]propyl}-1H-indole-3-carbonitrile;

kk) 5-[3-(4-pyrimidin-2-ylpiperazin-1-yl)propyl]-1H-indole-3-carbonitrile;

ll) 5-{3-[(2,3-dihydrobenzo[1,4]dioxin-2-ylmethyl)amino]propyl}-1H-indole-3-carbonitrile;

mm) 5-{3-[4-(3-methoxyphenyl)-3-methylpiperazin-1-yl]propyl}-1H-indole-3-carbonitrile;

nn) 5-{3-[4-(1-methyl-1H-imidazo[4,5-c]pyridin-4-yl)piperazin-1-yl]propyl}-1H-indole-3-carbonitrile;

oo) N-(4-{1-[3-(3-cyano-1H-indol-5-yl)propyl]piperidin-4-ylmethyl}-phenyl)acetamide;

pp) 5-{3-[4-(4-pyridin-3-ylthiazol-2-yl)piperazin-1-yl]propyl}-1H-indole-3-carbonitrile;

qq) ethyl 2-{4-[3-(3-cyano-1H-indol-5-yl)propyl]piperazin-1-yl}-thiazole-4-carboxylate;

rr) 5-{3-[3-(2-oxopyrrolidin-1-yl)propylamino]propyl}-1H-indole-3-carbonitrile;

ss) ethyl (6-{4-[3-(3-cyano-1H-indol-5-yl)propyl]piperazin-1-yl}-2-oxo-2H-chromen-3-yl)carbamate;

tt) 5-{3-[4-(3-amino-2-oxo-2H-chromen-6-yl)piperazin-1-yl]propyl}-1H-indole-3-carbonitrile;

uu) methyl (6-{4-[3-(3-cyano-1H-indol-5-yl)propyl]piperazin-1-yl}-2-oxo-2H-chromen-3-yl)carbamate;

vv) 2-{4-[3-(3-cyano-1H-indol-5-yl)propyl]-piperazin-1-yl}thiazole-4-carboxamide; or ww) 4-[3-(3-cyano-1H-indol-5-yl)propyl]piperazine-1-thiocarboxamide;

or a pharmaceutically acceptable salt, stereoisomer or mixture thereof.

2. A compound of formula Ia

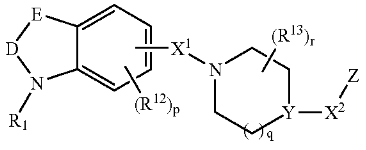

Ia wherein $R^1$ is H or $SO_2A$

A is straight-chain or branched alkyl having from 1 to 10 carbon atoms, alkenyl having from 2 to 10 carbon atoms or alkoxyalkyl having from 2 to 10 carbon atoms, and D-E is is $R^2C{=}CR^4$, wherein $R^2$ is H or methyl and $R^4$ is CN $X^1$ is $(CHR^7)_g$ g is 1, 2, 3, 4, 5 or 6, $R^7$ is, independently, has the meanings indicated for $R^2$ to $R^5$;

Y is CH or N, q is 0, p and r are each, independently of one another, 1, 2 or 3

Hal is F, Cl, Br or I, $R^{12}$ and $R^{13}$, are each, independently of one another, $R^4$ or are, independently of one another, Hal, CN, $NO_2$, $OR^6$, $N(R^6)_2$, $NO_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ or C(NH)NOH, and $X^2$-Z is at least one of

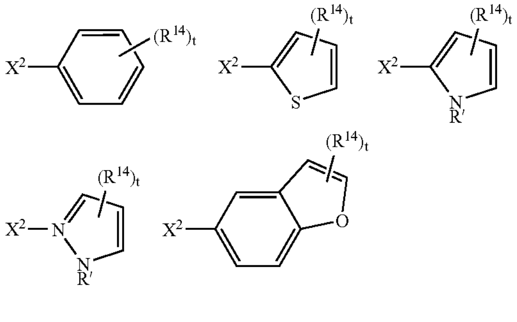

-continued

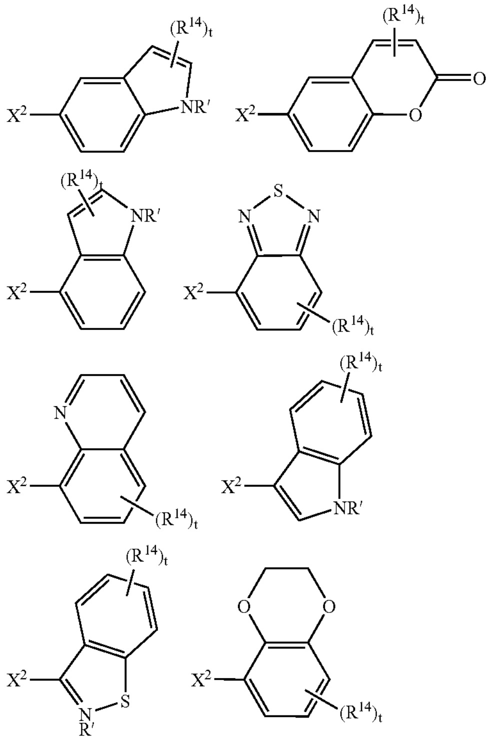

wherein $X^2$ is a bond, $R^{14}$ is, independently, Hal, A, $(CH_2)_n$Het, $(CH_2)_n$Ar, $(CH_2)_n$ $COO(CH_2)_m$Ar, $(CH_2)_nCOO(CH_2)_m$Het, $(CH_2)_n$ $OR^6$, $(CH_2)_nO(CH_2)_m$Ar, $(CH_2)_nO(CH_2)_m$Het, $(CH_2)_nN(R^6)(CH_2)_m$Ar, $(CH_2)_nN(R^6)(CH_2)_m$Het, $(CH_2)_nSO_2N(R^6)(CH_2)_m$Ar, $(CH_2)_nN(R^6)SO_2(CH_2)_m$ Ar, $(CH_2)_nSO_2N(R^6)(CH_2)_m$Het, $(CH_2)_nN(R^6)SO_2$ $(CH_2)_m$Het, $(CH_2)_nN(R^6)_2$, $(CH_2)_n$NHOA, $(CH_2)_n(R^6)$ Het, $(CH_2)_nOCOR^6$, $(CH_2)_nOC(O)N(R^6)_2$, $(CH_2)_nOC$ $(O)NR^6(CH_2)_m$Ar, $(CH_2)_nOC(O)NR^6(CH_2)_m$Het, $(CH_2)_nNR^6COOR^6$, $(CH_2)_nNR^6COO(CH_2)_m$Ar, $(CH_2)_n$ $NR^6COO(CH_2)_m$Het, or CN w is 0, 1, 2 or 3, t is 0, 1, 2, 3, 4 or 5, and m is 0, 1, 2, 3, 4, or 5 n is 0, 1, 2, or 3

R' is H, A, $(CH_2)_n$Het, $(CH_2)_n$Ar, cycloalkyl having from 3 to 7 carbon atoms or $SO_2A$;

or a pharmaceutically acceptable salt, stereoisomer, or mixture thereof.

3. A process for the preparation of a pharmaceutical composition, comprising converting a compound of claim 2 into a suitable dosage form together with at least one solid, liquid or semi-liquid excipient of adjuvant.

4. A pharmaceutical composition, comprising at least one compound of claim 2 and a pharmaceutically acceptable carrier.

5. A process for the preparation of a compound of formula Ia according to claim 2 or a salt thereof comprising reacting a) a compound of formula II

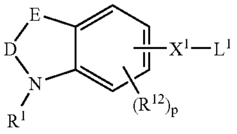

II wherein $L^1$ is Cl, Br, I, OH, a reactively esterified OH group or a diazonium group, and $R^1$, D, E, $R^{12}$, p and $X^1$ are as defined in claim 2, b) with a compound of formula IIIa

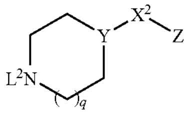

IIIa wherein $L^2$ is H or a metal ion, and $X^2$ and Z are as defined in claim 2, and optionally c) the resultant compound of formula Ia into a salt by treatment with an acid.

6. A compound of formula IIa

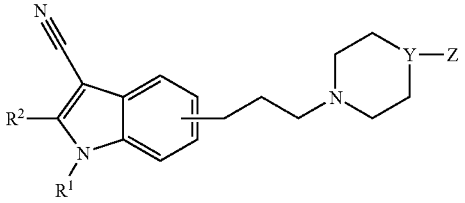

IIa wherein $R^1$ and $R^2$ are as defined in claim 2; and

Y-Z is a radical which is at least one of

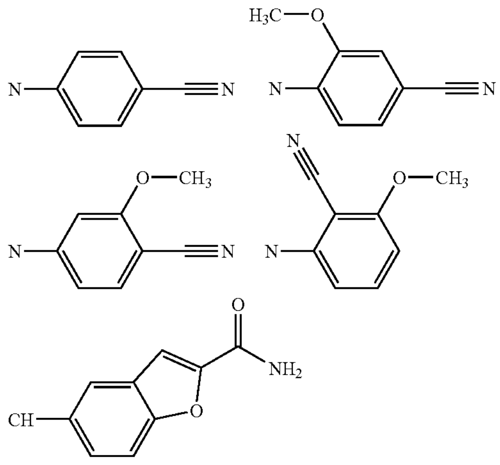

-continued

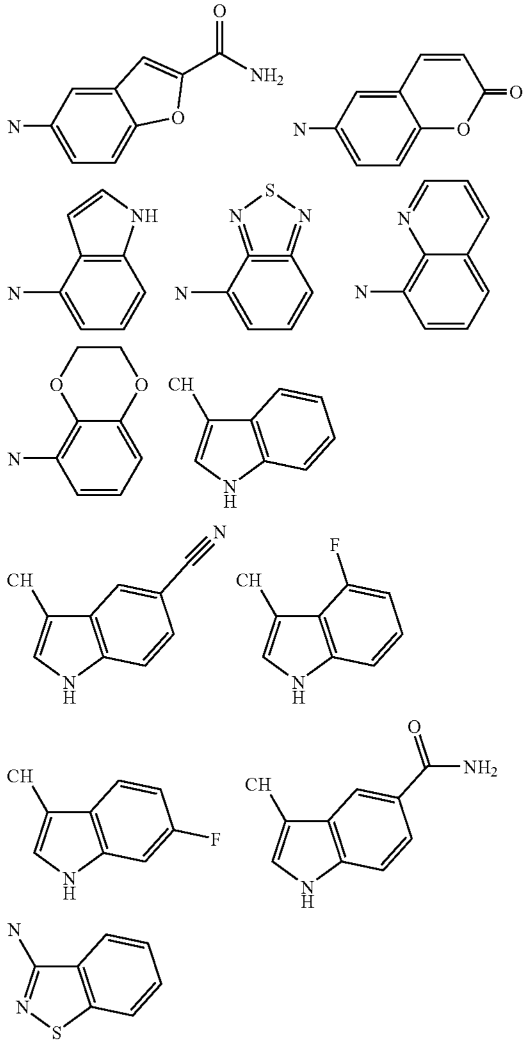

or a radical which is at least one of

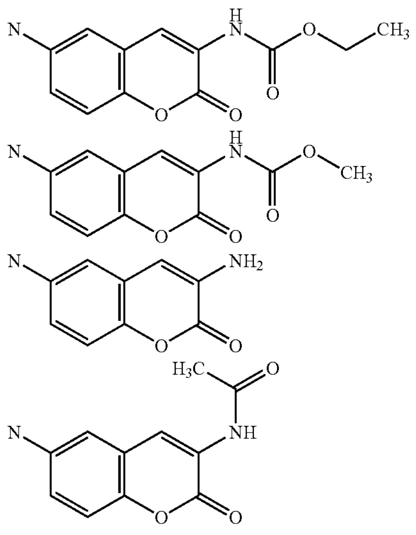

-continued

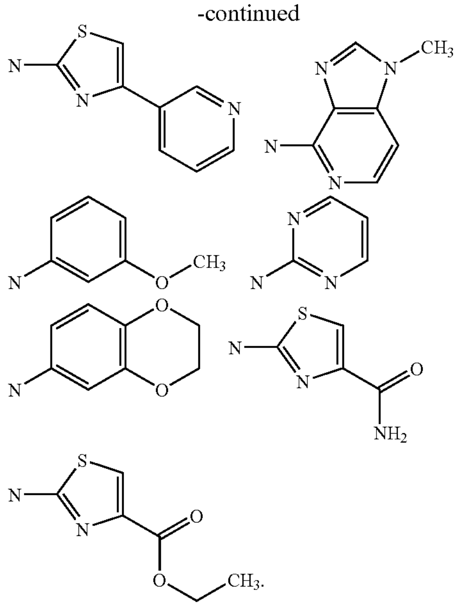

or a pharmaceutically acceptable salt, stereoisomer, or mixture thereof.

7. A compound of formula Ia according to claim 2

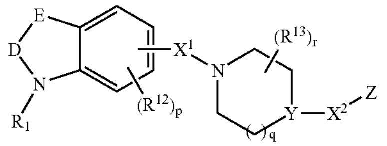

Ia wherein $R^1$ is H or A

A is straight-chain or branched alkyl having from 1 to 10 carbon atoms, alkenyl having from 2 to 10 carbon atoms or alkoxyalkyl having from 2 to 10 carbon atoms, and D-E is is $R^2C{=}CR^4$, wherein $R^2$ is H or methyl and $R^4$ is CN $X^1$ is $(CHR^7)_g$ g is 3, $R^7$, independently, has the meanings indicated for $R^2$ to $R^5$;

Y is CH or N, q is 0, p and r are, independently of one another, 0, 1, 2 or 3

Hal is F, Cl, Br or I, $R^{12}$ and $R^{13}$, are, independently of one another, Hal, CN, $NO_2$, $OR^6$, $N(R^6)_2$, $NO_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ or C(NH)NOH, and $X^2$-Z is at least one of

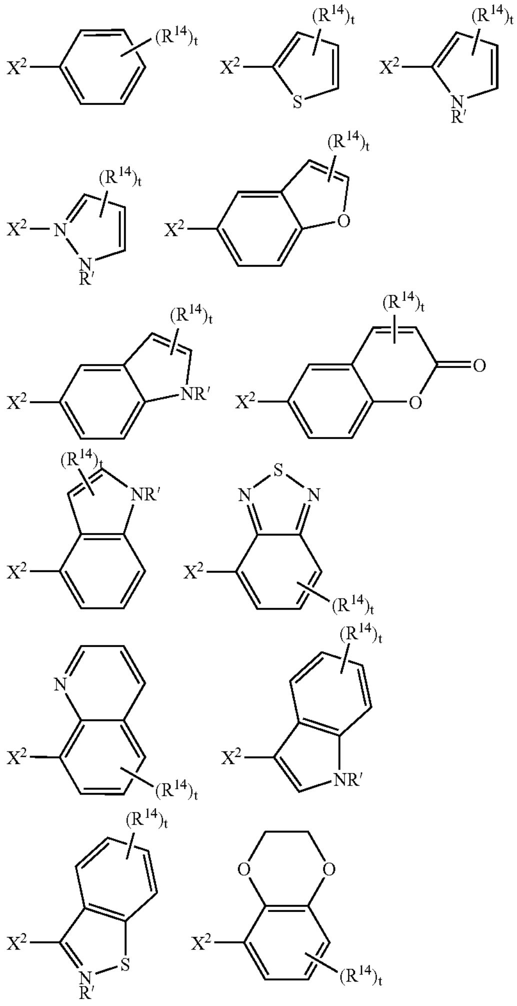

wherein $X^2$ is a bond, $R^{14}$ is, independently, Hal, $NO_2$, $OR^6$, $N(R^6)_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and/or C(NH)NOH, w is 0, 1, 2 or 3, t is 1, 2, 3, and R' is H, A, $(CH_2)_n$Het, $(CH_2)_n$Ar, cycloalkyl having from 3 to 7 carbon atoms or $SO_2A$;

or a pharmaceutically acceptable salt, stereoisomer, or mixture thereof.

* * * * *

UNITED STATES PATENT AND TRADEMARK OFFICE

CERTIFICATE OF CORRECTION

PATENT NO. : 7,572,796 B2
APPLICATION NO. : 10/511155
DATED : August 11, 2009
INVENTOR(S) : Schadt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this

Seventh Day of September, 2010

David J. Kappos
*Director of the United States Patent and Trademark Office*

UNITED STATES PATENT AND TRADEMARK OFFICE

CERTIFICATE OF CORRECTION

PATENT NO. : 7,572,796 B2
APPLICATION NO. : 10/511155
DATED : August 11, 2009
INVENTOR(S) : Schadt et al.

It is certified that error appears in the above-identified patent and that said Letters Patent is hereby corrected as shown below:

Column 63, line 45 reads "p and r are each, independently of one another, 1, 2 or 3" should read -- p and r are each, independently of one another, 0, 1, 2 or 3 --

Column 65, line 26 reads "$L^2$ is H or a metal ion, and $X^2$ and Z are as defined in claim" should read -- $L^2$ is H or a metal ion, and Q, Y, $X^2$ and Z are as defined in claim --

Column 65, line 30 reads "c) the resultant compound of formula Ia into a salt by" should read -- c) converting the resultant compound of formula Ia into a salt by --

Signed and Sealed this
Twenty-ninth Day of March, 2011

David J. Kappos
*Director of the United States Patent and Trademark Office*